(12) United States Patent
Torti et al.

(10) Patent No.: US 6,589,966 B1
(45) Date of Patent: Jul. 8, 2003

(54) CYTOTOXIC METAL CHELATORS AND METHODS FOR MAKING AND USING SAME

(75) Inventors: Suzy V. Torti, Winston-Salem, NC (US); Frank M. Torti, Winston-Salem, NC (US); Roy P. Planalp, Portsmouth, NH (US); Martin W. Brechbiel, Annandale, VA (US)

(73) Assignees: Wake Forest University Health Sciences, Winston-Salem, NC (US); University of New Hampshire, Durham, NH (US); National Institutes of Health, Bethesda, MD (US)

( * ) Notice: Subject to any disclaimer, the term of this patent is extended or adjusted under 35 U.S.C. 154(b) by 0 days.

(21) Appl. No.: 09/646,428

(22) PCT Filed: Mar. 18, 1999

(86) PCT No.: PCT/US99/05977
§ 371 (c)(1),
(2), (4) Date: Sep. 18, 2000

(87) PCT Pub. No.: WO99/47502
PCT Pub. Date: Sep. 23, 1999

Related U.S. Application Data

(60) Provisional application No. 60/090,618, filed on Jun. 25, 1998, and provisional application No. 60/078,448, filed on Mar. 18, 1998.

(51) Int. Cl.[7] .............. A61K 31/44; C07D 401/02

(52) U.S. Cl. ................. 514/332; 546/264

(58) Field of Search .............. 546/264; 514/332

(56) References Cited

U.S. PATENT DOCUMENTS

| 5,430,058 A | 7/1995 | Shanzer et al. |
| 5,446,145 A | 8/1995 | Love et al. |

FOREIGN PATENT DOCUMENTS

| WO | WO 9602531 A1 | 2/1996 |
| WO | WO 97/49401 | 12/1997 |

OTHER PUBLICATIONS

Bollinger, J. et al., Lipophilic Hexadentate Aluminum, Gallium, Indium, and Iron Complexes of a New Phenolate–D-erivatized Cyclohexanedtriamine Ligand. *Inorg. Chem.* 33:1241 (1994).

Bowen, T. et al., An Improved Synthesis of cis,cis–1,3,5–Triaminocyclohexane. Synthesis of Novel Hexadentate Liqand Derivatives for the Preparation of Gallium Radiopharmaceuticals. *Bioorg. Med. Chem. Lett.* 6:807 (1996).

Breuer, W. et al., Iron Acquired from Transferrin by K562 Cells Is Delivered into a Cytoplasmic Pool of Chelatable Iron(II). *J. Biol. Chem.* 270:24209 (1995).

Brüggeman, S. et al., Ifosfamide Cytotoxicity on Human Tumor and Renal Cells: Role of Chloroacetaldehyde in Comparison to 4–Hydroxyifosfamide. *Cancer Res.* 57:2676 (1997).

Chitambar, C. et al., Evaluation of Continuous–Infusion Gallium Nitrate and Hydroxyurea in Combination for the Treatment of Refractory Non–Hodgkin's Lymphoma. *Amer. J. Clin. Oncol.* 20(2):173 (1997).

Chum, H.L. et al., Tris(2–(aminomethyl)pyridine)iron(II): A New Spin–State Equilibrium in Solution. *Inorg. Chem.* 21:1146 (1982).

Donfranesco, A. et al., Role of Deferoxamine in Tumor Therapy. *Acta, Haematol.* 95:66 (1996).

Drago, R.S., Chapter 12—Factors Affecting Nuclear Relaxation in Paramagnetic Systems. *Physical Methods for Chemists*, Saunders, pp519 (1992).

Frantz, C., Dose Escalation Study of Desferrioxamine (DFO) in Children with Refractory Neuroblastoma. *Proc. Acad. Soc. Clin. Oncol.* 416 (abstr) (1994).

Goedken, V.L. et al., Facile Promotion of Oxidative Dehydrogenation by Irons Ions and the Synthesis of New Complexes of Iron with Highly Unsaturated Tetraaza Macrocycles. *J. Am. Chem. Soc.* 94:7355 (1972).

(List continued on next page.)

Primary Examiner—Zinna Northington Davis
(74) Attorney, Agent, or Firm—Kilpatrick Stockton LLP

(57) ABSTRACT

A family of hexadentate Fe(II) chelators having marked antiproliferative activity against tumor cells is disclosed. The cytotoxic metal chelators and complexes of the present invention are represented by the general formula below:

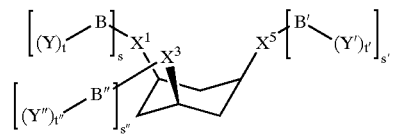

wherein:
$X^1$, $X^3$, and $X^5$ are N, O or S, wherein the $X^1$, $X^3$, and $X^5$ atoms are at the 1, 3, and 5 positions of a cyclohexyl group and are in a cis, cis disposition;

B, B', and B" are aliphatic, branched aliphatic, or aryl groups, or any combination thereof, wherein the number of atoms between X and Y is about 2 to about 4;

Y, Y' and Y" contain N, O, or S atoms that originate from either aliphatic, branched aliphatic, aryl, or heterocyclic groups, or any combination thereof, and/or Y, Y' and Y" are $NH_2$ or NHR, OH, or SH, $CO_2H$, $P(O)(OH)_2$, RP(O)OH, ROP(O)OH groups or a combination thereof, and R is H, aliphatic, branched aliphatic, or aryl groups, or any combination thereof that may or may not be identical in Y, Y' and Y";

s, s', and s" are 0 to about 2; and t, t', and t" are 0 to about 2. Application of the metal chelators of the present invention as chemotherapeutic agents is also disclosed.

35 Claims, 17 Drawing Sheets

OTHER PUBLICATIONS

Goto, M. et al., Dependence of Dehydrogenation of Amines towards Coordination Geometry: Oxidation Products of Tricyano[di(2–pyridylmethyl)amine]ferrate(II) from mer and fac isomers. *J. Chem. Soc.*, Chem. Commun. 2015 (1994).

Hegetschweiler, et al., 1,3,5–Trideoxy–1,3,5–tris (2–hydroxybenzyl)amino)–cis–inositol, a Novel Multidentate Ligand Providing Various N,O Coordination Sites. Structure of the Rhenium(V) Complex. *Inorg. Chem.* 31:4027 (1992).

Hilfiker, K.A. et al., Tricationic Metal Complexes ([ML] $[NO_3]_3$, M=Ga, In) of N,N',N"–Tris (2–pyridylmethyl-)–cis–1,3,5–triaminocyclohexane: Preparation and Structure. *Inorg. Chem.* 36:4600–03 (1997).

Hoffbrand, A., Prospects for Oral Iron Chelation Therapy. J *Lab. Clin. Med.* 123:492 (1994).

Holanda, MID et al., Transamination and Amine–Exchange Reactions in the System Iron (II)–Sodium Pyruvate–Aminomethylpyridine. I. Stoichiometry and Reaction Products. *Inorg. Chem.* 15:890–93 (1976).

Keene, F.R. et al., Investigations of the Nature of Dehydrogenation of the α–Carbon Atom in the Oxidation of Amines Coordinated to Ruthenium. *J. Am. Chem. Soc.* 105:7075 (1983).

Lions et al., Sexadentate Chelate Compounds. *J. Am. Chem. Soc.* 79:1572 (1957).

Loebstein, R., *Clin. Drug. Invest.*, 13(6):345–349 (1997).

Mansour, A.N. et al., FE(III) ATP Complexes—Models for Ferritin and Other Polynuclear Iron Complexes with Phosphate. *J. Biol. Chem.* 260:7975 (1985).

March, J., Reactivity. *Advanced Organic Chemistry*, McGraw–Hill, pp 914 ff.

Miller, R., Chemotherapy of Advanced Transitional–Cell Carcinoma of the Bladder. *Cancer Chemotherapy, and Pharmacology* 30 Suppl. S99 (1992).

Mosmann, T., Rapid Colorimetric Assay for Cellular Growth and Survival: Application to Proliferation and Cytotoxicity Assays. *J. Immunol. Meth.* 65:55 (1983).

Nathan, D., An Orally Active Iron Chelator. *N. Eng. J. Med.* 332(14) (1995).

Olivieri, N., Iron–Chelation Therapy with Oral Deferiprone in Patients with Thalassemia Major. *N. Engl. J. Med.* 14:918 (1995).

Paul–Roth, C. et al., Amide Functional Group Contribution to the Stability of Gadolinium(III) Complexes: DTPA Derivatives. *Inorg. Chem.* 34:1408 (1995).

Richardson, D. et al., The Potential of Iron Chelators of the Pyriodaxal Isonicotinoyl Hydrazone Class as Effective Antiproliferative Agents. *Blood* 86:4295 (1995).

Seligman, P. et al., Treatment with Gallium Nitrate: Evidence for Interference with Iron Metabolism in Vivo. *Amer. J. Hematol.* 41:232 (1992).

Seymour, G., Transferrin Receptor Expression by Human Bladder Transitional Cell Carcinomas, *Urol. Res.* 15:341 (1987).

Shannon, R.D., Revised Effective Ionic Radii and Systematic Studies of Interatomic Distances in Halides and Chalcogenides. *Acta Cryst.*, A32, 751 (1976).

Silber, R., Chemosensitivity of Lymphocytes from Patients with B–Cell Chronic Lymphocytic Leukemia to Chlorambucil, Fludarabine, and Camptothecin Analogs. *Blood* 84:3440 (1994).

Torti, S. et al., The Molecular Cloning and Characterization of Murine Ferritin Heavy Chain, a Tumor Necrosis Factor–Inducible Gene. *J. Biol. Chem.* 263:12638 (1988).

Bollinger, J. et al., Lipophilic Hexadentate Gallium, Indium And Iron Complexes Of New Phenolate–derivatized Cyclohexanetriamines As Potential In Vivo Metal–transfer Reagents. *J. Chem. Soc.*, Dalton Trans. 1995, pp. 1677–1688.

Caravan, P. et al., Tripodal Aminophenolate Ligand Complexes Of Aluminum (III), Gallium (III), and Indium (III) In Water. *Inorg. Chem.*, 36:2, 1997, pp. 236–248.

Cronin, L. et al., Preparations And Structures Of Two cis,cis–1,3,5–Triaminocyclohexane–Based Complexes Containing Hydrogen–bonded Solvent Molecules. *J. Chem. Soc., Dalton Trans.* 1996. pp. 3337–3339.

Cronin, L. et al., Syntheses And Single–Crystal X–ray Structures Of A Series Of Monosubstituted cis,cis–1,3, 5–Triaminocyclohexane–Based Complexes. *Inorg. Chem.*, 36:12, 1997, pp. 2594–2600.

Grimes, J. et al., The Stabilities Of The Alkaline Earth Chelates Of Some Polyaminopolycarboxylic Acids. *J. Inorg. Nucl. Chem.*, vol. 36, 1963, pp. 1225–1238.

Kabachnik, M. et al., Synthesis and *Complexing* Properties of cis,cis–1,3,5–[2–(diphenylphosphinyl) ethylamino] Cyclohexane. Chemical Abstracts Service, Columbus, OH, 1993.

Park, G. et al., Novel Iron Complexes And Chelators Based On cis,cis–1,3,5–Triaminocyclohexane: Iron–Mediated Ligand Oxidation And Biochemical Properties. *J. Biol. Inorg. Chem.* 3:5, 1998, pp. 449–457.

Zompa, L.J., Stability Constants For Some Metal Complexes Of cis,cis–1,3,5–Triaminocyclohexane-N,N', N"–triacetic Acid. *Inorg. Chem.*, 10:12, 1971, pp. 2647–2649.

Supplementary Partial European Search Report for EP 99 91 3968 Mailed Jan. 18, 2002.

tachpyr, open conformation tachpyr, closed conformation

PIH

Desferrioxamine (DFO)

L1, R = Me; CP94, R = Et

Metal complexes of tachpyr tachquin tach-C(Me)-pyr (R = Me)
tachpyr (R = H)

tach-6-Mepyr

S,S,S-tachen-2-Bn
(also termed tachbn)

S,S,S-tachen-2-Me
(also termed tachpn)

tachen-OH tachcarbox (N-R)$_3$tachpyr, R = Me or Et

Scheme 3

Scheme 2 a)

ampy (excess)

b)

CYTOTOXIC METAL CHELATORS AND METHODS FOR MAKING AND USING SAME

RELATED PATENT APPLICATIONS

This application is a 371 application of PCT/US99/05977 filed Mar. 18, 1999, which claims the benefit of U.S. Provisional Application Serial No. 60/078,448 filed Mar. 18, 1998 and U.S. Provisional Application Serial No. 60/090,618 filed Jun. 25, 1998.

STATEMENT REGARDING FEDERALLY SPONSORED RESEARCH

This invention was made with U.S. government support from a grant funded by the National Institute of Health DK 42412 and DK 42412-0951. The U.S. government may have certain rights in the invention.

BACKGROUND OF THE INVENTION

The present invention relates to chelators and their use as therapeutic agents. More particularly, the present invention relates to metal chelators and their use as chemotherapeutic agents in the treatment of cancer.

Biomolecules responsible for oxygen transport, electron transport, oxidation, reduction, and diverse other functions contain iron ("Fe") at their active sites. Iron is also essential for the catalytic activity of numerous critical enzymes, including respiratory chain enzymes and ribonucleotide reductase. Ribonucleotide reductase catalyzes the reduction of ribonucleotides to deoxynucleotides, the rate limiting step in DNA synthesis. Given the role of iron at the cellular level, in particular DNA synthesis, modulation of iron metabolism at the cellular level may play a key role in the treatment of various pathological conditions, for example, systemic iron overload and oxidative stress.

Iron deprivation strategies may indeed be useful in the treatment of cancer, a disease characterized by uncontrolled cell division. In fact, several strategies have been explored for applying iron deprivation therapy to treat cancer. For example, antibodies against transferrin receptors, which are responsible for the cellular uptake of circulating iron, have been used in the treatment of both hematopoetic and non-hematopoetic tumors. Gallium nitrate, which binds to the transferrin receptor, has been studied for use in the treatment of lymphoma and bladder cancers [Miller, R., *Cancer Chemotherapy, and Pharmacology* 30 *Suppl.* S99 (1992); Chitambar, C., *Amer. J. Clin. Oncol.* 20:173 (1997)]. Bladder cancer has been studied as a potential clinical target of iron depletion therapy [Seymour, G., *Urol. Res.* 15:341 (1987); and Seligman, P.,*Amer. J. Hematol.* 41:232 (1992)].

Iron chelators have been used diagnostically and as agents in the treatment of various disorders. Iron chelators are molecules that bind tightly to metal ions, rendering them chemically inert. The chemical bond formed between the chelator and the metal involves the donation of electrons present in the molecular orbital of the chelator to the vacant metal orbital. In general, a chelator can be characterized by the identity and number of donor atoms it contains, and its binding geometry. The most stable chelator metal complexes, or chelates, are formed when the denticity of the chelator is sufficient to coordinately saturate the metal. Iron occurs as a di- or trivalent cation with a coordinate number of six. Thus, stable iron chelators are advantageously hexadentate.

Iron chelators are commonly used to treat iron overload associated with genetic disorders and transfusion-dependent anemias (see U.S. Pat. No. 5,430,058). Iron chelators have also been used as contrast agents for diagnostic imaging, including X-ray and ultrasound, radiotherapy, and heavy metal detoxification (see U.S. Pat. No. 5,446,145). However, iron chelators have been developed primarily for use as agents to treat iron overload, and their effectiveness as well as the theories for their development have been based on this application. For this application, the desirable characteristics for iron chelators include chelation of Fe(III) with high stability, ability to mobilize iron for excretion, oral availability, and low chronic toxicity.

Representative iron chelators for the treatment of iron overload include members of the following five classes: hydroxamates, amine carboxylates, catechols, hydroxypyridinones and pyridoxal isonicotinoly hydrazones. Desferrioxamine (DFO), a member of the hydroxamate class of iron chelators, is the present clinical standard for the treatment of iron overload. DFO fulfills some but not all of the above-mentioned criteria for the treatment of iron overload. In particular, DFO exhibits a high and selective affinity for Fe(III). DFO is hexadentate so its effectiveness in binding iron is only weakly dependent on its concentration [Nathan, D., *N. Eng. J. Med.*332(14) (1995)]. DFO is also able to mobilize iron for excretion. However, DFO suffers from serious limitations. Like most hydorxymates, DFO is acid labile, displays some chronic toxicity, and cannot be given orally. Parenteral administration is required, causing both compliance problems and further limiting the drug's utility in third world nations where iron overload is common, and facilities and supplies for parenteral administration are lacking. Further, the high cost of DFO, which must be isolated from Streptomyces cultures, further limits this drug's utility [Hoffbrand, A., *J. Lab. Clin. Med* 123:492 (1994)].

The hydroxypyridinone family of chelators has recently been developed, and is currently being used in clinical trials for the treatment of iron overload. Deferiprone, also known as LI (a 1,2 dimeth-3-hydroxypyrid-4,1 compound), is a hydroxypyridinone, which has been the target of considerable study. Deferiprone is an orally active iron chelator [Olivieri, N., *N. Engl. J. Med* 14:918–922 (1995)] that mobilizes iron. However, deferiprone's affinity for Fe(III) is only moderate, and this affinity has a strong dependence on the concentration of deferiprone [Loebstein, R., *Clin. Drug. Invest,* 13(6):345–349 (1997)]. Deferiprone has its limitations. Generally, deferiprone has a much lower therapeutic ratio than DFO. It is considerable more toxic, and has known serious side effects including agranulocytosis.

Another class of iron chelators, pyridoxal isonicotinoyl hydrazone (PIH) and its derivatives, has also been studied. PIH derivatives and their iron complexes exhibit good intracellular mobility, but their affinity for Fe(III) is only moderate [PCT WO 960253 1, Jul. 10, 1995].

Chemotherapeutic agents which exploit iron deprivation mechanisms represent a relatively unexplored field of study. These agents are considered antimetabolites, since they interfere with DNA synthesis. Some iron(III) chelators have also been studied for use as chemotherapeutic agents. Desferrioxamine (DFO) is currently being tested in clinical trials as a combination chemotherapeutic agent for treating neuroblastoma and prostate cancer [Donfranesco, A., *Acta, Haematol.* 95:66 (1996); and Frantz, C., *Proc. Acad. Soc. Clin. Oncol.:* 416 (abstr) (1994)]. Chelators of the pyridoxal isonicotinoyl hydrazide (PIH) family have also been studied as anti-proliferative agents. Members of the PIH family are tridentate ligands having both oxygen and nitrogen donor atoms. Several members of the PIH family have been identified with an $IC_{50}$ (1–7 $\mu$M) lower than desferioxamine (70 μM), and a potential correlation between lipophilicity and cytotoxicity [Richardson, D., *Blood* 86:4295 (1995)].

Most chelators selectively favor iron (III), ("Fe (III)"), due to the stronger binding and lower toxicity of iron (III) over iron (II), ("Fe(II)"). While all of the above chelators bind iron(III), chelators of iron(II) are relatively unexplored due in part to their relative lack of metal specificity and the potential toxicity of Fe(II). Fe(II) may reduce $H_2O_2$, resulting in the production of the highly reactive, tissue-damaging hydroxyl radical. Not all chelators yield toxic Fe(II) complexes, however, because structural features of the chelator, such as steric effects, may interfere in the mechanism of hydroxyl radical formation. Also, a chelator such as phenanthroline affords a redox potential of Fe(II) (+1.15 V/NHE) too positive to allow reduction of $H_2O_2$.

Chelators of iron(II) that are redox-active may also draw on bound iron(II), if they can reduce it to iron(II). The property of redox may, therefore, confer advantages on iron(II) chelators relative to iron(III) chelators for several reasons. First, there is a pool of intracellular iron accessible to iron(II) chelators, and, second, there are cellular stores of iron(III) that may be accessed by reduction to iron(II). Thus, there is a need for chelators of greater versatility, that may access both Fe(III) and Fe(II), for clinical use.

One substance, bipy, has been found to be an intracellular chelator of Fe(II) in the treatment of vasospasm [Horky et al., PCT WO 97/49401, Dec. 31, 1997]. It is believed that this chelator functions through weak complexation of Fe(II), which allows open coordination sites to facilitate delivery of nitric oxide to walls of blood vessels. This weak complexation of Fe(II) is not suitable for action as an iron deprivation agent. Further, bipy has demonstrated only weak cytotoxic effects on tumor cells.

Another substance with Fe(II) chelating and redox properties is tachpyr. Initially discovered and synthesized by several co-inventors of the present application, tachpyr reacts with Fe(II), and causes a state of cellular iron deprivation. Tachpyr is more effective than bipy because it is a hexadentate chelator, while bipy is bidentate. Thus, tachpyr's effectiveness as an Fe(II) chelator is independent of its concentration. Tachpyr exhibits redox properties, and binds Fe(III) through reduction to Fe(II). Tachpyr stoichiometrically forms hydroxyl radicals from hydrogen peroxide. The reductive capture of Fe(III) is believed to occur via oxidation of tachpyr to a new imine ligand, "tachpyr-$nH_2$" (n=1, 2,3), with concomitant reduction of Fe(III) to complexed Fe(II), "Fe[tachpyr-$nH_2$]$^{2+}$".

More recently, three oxygen donor groups were added to tach. The resulting chelators bind Al(III), Ga(III) and Fe(III), but no interaction with Fe(II) is described or expected [Bollinger, J. et al., *Inorg Chem* 33, 1241 (1994)]. 1,3,5-Triamino-1,3,5-trideoxy-cis-inositol is a tridentate chelator similar to tach. Very few hexadentate derivatives of this substance have been prepared [Hegetschweiler, et al., *Inorg Chem* 31, 4027 (1992)].

One of the compounds of tachpry is cis-cis-1,3,5-triaminocyclohexane or "tach." Tach, a tridentate ligand, has been known for some time. Addition of three donor groups to tach forms a hexadentate ligand. A very small number of such hexadentate derivatives were known prior to this invention. Tachimpyr and Fe[tachimpyr]$^{2+}$ were prepared, and not further studied [Lions et al., *J. Am. Chem. Soc.* 79,1572 (1957)].

There are several potential problems with the chemistry of Fe[tachpyr-$nH_2$]$^{2+}$ that may limit its iron deprivation effects and, therefore, its cytotoxicity. Fe[tachpyr-$nH_2$]$^{2+}$ and other imine complexes may be attacked by nucleophiles, leading to release of Fe. This problem is related to the susceptibility of imino groups to hydrolysis. Thus, the free chelator tachpyr-$3H_2$ has no cytotoxicity, and is unstable in aqueous medium. Another significant issue with Fe[tachpyr-$H_2$]$^{2+}$ is its charge of +2. A positive charge generally restricts the penetration of biological membranes. Thus, tachpyr is unlikely to mobilize intracellular iron, due to inability of Fe[tachpyr-$nH_2$]$^{2+}$ to cross cell membranes. A positive charge also facilitates reactivity with biologically available anions such as chloride or hydroxide. Thus, for reasons of charge (+2) and chemical structure (imino groups), tachpyr-$nH_2$ has intrinsic limitations in its action as an iron deprivation agent.

While chemotherapeutic agents have been in use for over fifty years, the search for new anti-cancer drugs is ongoing. There remains a general need for alternative agents, and more particularly, iron deprivation chemotherapeutic agents with novel cytotoxic mechanisms. This is so because anti-cancer drugs, which exploit different cytopathic mechanisms, can be used in combination to achieve maximum tumor effect with minimal toxicity.

SUMMARY OF THE INVENTION

The present invention is directed to a novel family of metal chelators and their metal complexes. The metal chelators are further characterized as hexadentate, chemical compounds that bind iron relatively independent of concentration, and cross the cell membrane to chelate intracellular iron pools. The metal chelators comprise a varying number of chelating moieties attached to a linking group. The chelating moiety is a linear or cyclic hydrocarbon, which is substituted at one or more carbons with a donor atom, and the linking group is substituted at one or more positions by a donor atom. The metal chelators of the present invention are represented by the general formula below:

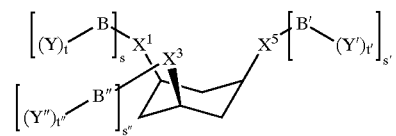

wherein:
X$^1$, X$^3$, and X$^5$ are N, O or S, such at the X$^1$, X$^3$, and X$^5$ atoms are at the 1, 3, and 5 positions of a cyclohexyl group and are in a cis, cis disposition;

B, B', and B" are aliphatic, branched aliphatic, or aryl groups, or any combination thereof, wherein the number of atoms between X and Y is about 2 to about 4;

Y, Y' and Y" contain N, O, or S atoms that originate from either aliphatic, branched aliphatic, aryl, or heterocyclic groups, or any combination thereof, and/or Y, Y' and Y" are $NH_2$ or NHR, OH, or SH, $CO_2H$, $P(O)(OH)_2$, RP(O)OH, ROP(O)OH groups or any combination thereof, and R is H, aliphatic, branched aliphatic, or aryl groups, or any combination thereof that may or may not be identical in Y, Y' and Y";

s, s', and s" are 0 to about 2; and t, t', and t" are 0 to about 2.

The present invention is also directed to pharmaceuticals including chemotherapeutic agents, comprising as active ingredients the metal chelators of the general formula described above as well as the embodiments which are described below. The antiproliferative activity exhibited by the present compounds is consistent with their utility as chemotherapeutic agents. While various modes of administration are contemplated for the metal chelators as pharmaceuticals, oral administration is the preferred route of administration. The compositions can be orally administered by incorporating them with a liquid diluent or a solid carrier. As a pharmaceutical, the composition of the present invention can be used to reduce the level of iron in cells in need of such a reduction. In one embodiment, the composition of the present invention is used to inhibit tumor cell growth. While the composition of the present invention is used in the therapeutic reduction of iron, the composition may also be used to remove other metals present in amounts in need of reduction.

The metal chelators of the present invention are distinguishable in several ways from known cytotoxic iron chelators such as DFO and PIH in both their chemical structure and physical properties. The present metal chelators are characterized by a donor atom in the linking group as well as in the attached chelating moieties. The metal chelators are hexadentate ligands with profound cytotoxicity to tumor cells. While oral administration is preferable for these compounds, it is contemplated that other forms of administration may be used. The cytotoxic mechanism for the present compounds is believed to include intracellular iron chelation. Further, the chemical properties of the present compounds may allow them to bind as well as to reduce iron, which profoundly influences their biological activity.

The metal chelators of the present invention provide significant advantages and innovations in design over tach-pyr and over other chelators mentioned above in a number of ways. For example, chelator tach-C(Me)-pyr (R=Me), shown in FIG. 2, is intended to provide greater redox activity relative to tachpyr, in its ability to reductively capture Fe(III). Thus, Fe[tach-C(Me)-pyr-nH$_2$]$^{2+}$ forms with greater facility relative to Fe[tachpyr-nH$_2$]$^{2+}$. It also provides steric hindrance to prevent the hydrolysis of imino groups, leading to the loss of Fe. S,S,S-tachen-2-Bn (FIG. 3) and S,S,S-tachen-2-Me (FIG. 3) are chelators with primary amino groups, which are better donors to Fe(II) relative to Fe(III). Greater basicity may also lead to greater affinity for Fe(II) relative to the pyridyl group of tachpyr. Chelators with a predicted greater mobility of their Fe complexes include tachcarbox, R=Me or Et (FIG. 4). This ligand will form neutral or anionic complexes with iron, which will facilitate iron mobilization.

Another property shared by the novel metal chelators tachen-OH (FIG. 4) and tachcarbox, R=Me or Et (FIG. 4) is versatility in the binding of both oxidation states of iron. Through incorporation of both nitrogen and oxygen donor atoms, which have affinity for Fe(II) and Fe(III), respectively, tachen-OH and tachcarbox, R=Me or Et may access both biologic forms of iron. Intracellular penetrating ability of the free chelators is often related to their lipophilicity. The donor atoms of tachquin (FIG. 2), are similar to tachpyr, but the additional aromatic rings of the quinoline group increase lipophilicity. Tach-6-Mepyr (FIG. 2) is another such chelator, which has 6-methyl groups to provide greater lipophilicity relative to tachpyr.

The effectiveness of the iron complexes in producing injurious hydroxyl radicals may also be enhanced relative to tachpyr. Thus, Fe-tachcarbox complexes may have a more negative redox potential relative to Fe(tachpyr-nH$_2$), allowing more efficient cycling of Fe(III)-Fe(II) to produce hydroxyl radicals.

The chelators (N—R)$_3$tachpyr, R=Me or Et (FIG. 4) demonstrate low toxicity in this family of compounds, in that they are not effective chelators of Fe(II), nor are they cytotoxic or antiproliferative agents, yet they share some of the same moieties in their structure.

A preferred embodiment of the metal chelators of the present invention is represented by the following chemical formula:

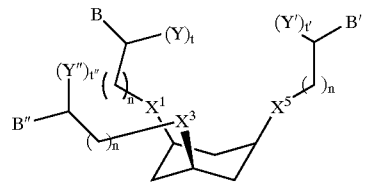

wherein:

X$^1$, X$^3$, and X$^5$ are N, O or S, such at the X$^1$, X$^3$, and X$^5$ atoms are at the 1, 3, and 5 positions of a cyclohexyl group and are in a cis, cis disposition;

B, B', and B" are aliphatic, branched aliphatic, or aryl groups, or any combination thereof, wherein the number of atoms between X and Y is about 2 to about 4;

Y, Y' and Y" contain N, O, or S atoms that originate from either aliphatic, branched aliphatic, aryl, or heterocyclic groups, or any combination thereof, or NH$_2$ or NHR, OH, or SH, CO$_2$H, P(O)(OH)$_2$, RP(O)OH, ROP(O)OH groups or any combination thereof, and R is H, aliphatic, branched aliphatic, or aryl groups, or any combination thereof that may or may not be identical in Y, Y' and Y";

t, t', and t" are 0 to about 2; and n is between 0 and about 3.

In yet another preferred embodiment, the metal chelators are represented by the following chemical formula:

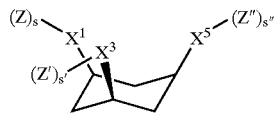

wherein:

X$^1$, X$^3$, and X$^5$ are N, O or S, such at the X$^1$, X$^3$, and X$^5$ atoms are at the 1, 3, and 5 positions of a cyclohexyl group and are in a cis, cis disposition; and s, s', s" are 0 to about 2;

and Z, Z', Z" = 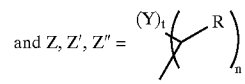

wherein:

R is H, aliphatic, branched aliphatic, or aryl groups, or any combination thereof that may or may not be identical in Z, Z' and Z";

Y is NH$_2$ or NHR', OH, or SH, CO$_2$H, P(O)(OH)$_2$, RP(O)OH, R'OP(O)OH groups, or a combination of these is R' is H, aliphatic, branched aliphatic, or aryl groups, or any combination thereof, or Y is a group containing N, O, or S atoms that originate from either aliphatic, branched aliphatic, aryl, heterocyclic groups, or any combination thereof, in any case, Y and R' may or may not be identical in Z, Z' and Z";

t is 0 to about 2;

n is between 0 and about 3.

In yet another preferred embodiment, a pharmaceutical composition for treating and preventing medical conditions in mammals is disclosed, comprising as active ingredient a compound of the formula:

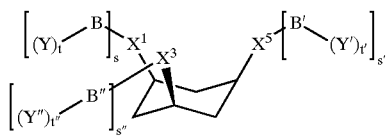

wherein:
- $X^1$, $X^3$ and $X^5$ are N, O or S, such at the $X^1$, $X^3$, and $X^5$ atoms are at the 1, 3, and 5 positions of a cyclohexyl group and are in a cis, cis disposition;
- B, B', and B" are aliphatic, branched aliphatic, or aryl groups, or any combination thereof, wherein the number of atoms between X and Y is about 2 to about 4;
- Y, Y' and Y" contain N, O, or S atoms that originate from either aliphatic, branched aliphatic, aryl, or heterocyclic groups, or a combination thereof, and/or Y, Y' and Y" are $NH_2$ or NHR, OH, or SH, $CO_2H$, $P(O)(OH)_2$, $RP(O)OH$, $ROP(O)OH$ groups or a combination thereof, and R is H, aliphatic, branched aliphatic, or aryl groups, or a combination thereof that may or may not be identical in Y, Y' and Y";
- s, s', and s" are 0 to about 2; and
- t, t', and t" are 0 to about 2.

The pharmaceutical composition comprises an active ingredient compound, which is selected from the group of metal chelators consisting of tach-C(Me)pyr, tach-6-Mepyr, tachquin, sss-tachem-2Bn, sss-tachen-2Me, (N—R)$_3$tachpyr, tachpyr-2H$_2$ and tach-N-Me-Im-imine. The pharmaceutical composition can be formulated in a therapeutic dosage by itself, in combination with at least one other pharmaceutical, or chemically linked to at least one other pharmaceutical. The composition can be combined with pharmaceutically acceptable carriers, diluents, stabilizers, solubilizers, lubricants, binders and the like or excipients thereof. Further, the pharmaceutical composition comprises a mammalian metabolic conjugate of the active ingredient compound.

It is contemplated that the pharmaceutical composition can be used in the treatment and prevention of the following medical conditions including, but are not limited to, cancer, inflammatory and infectious conditions, vasoreactive and vasoocclusive conditions, coronary and peripheral athlerosclerosis, parasitic diseases, neurologic and neuromuscular conditions, and viral conditions including AIDS. Additional medical conditions further include vasospasm, Parkinson's disease, Alzeihmer's disease, malaria, tuberculosis, arthritis, allergic and asthmatic conditions, hepatitis, coronary and peripheral vascular ischemia-reperfusion injury of blood vessels.

In another embodiment, the pharmaceutical composition is orally formulated in combination with a liquid diluent or a solid carrier.

In yet another embodiment, the pharmaceutical composition is administered in a therapeutically effective dosage, which prevents the occurrence of, reduces the rate of growth of, or diminishes the size of tumor cells or any combination therof.

The preceding and further objects of the present invention will be appreciated by those of ordinary skill in the art from a reading of the detailed description of the invention and preferred embodiments which follow, such description being merely illustrative of the present invention.

BRIEF DESCRIPTION OF THE DRAWINGS

The invention will be better understood after a reading of the following description of the invention when considered with the drawings.

DETAILED DESCRIPTION OF THE INVENTION

Figure 1:
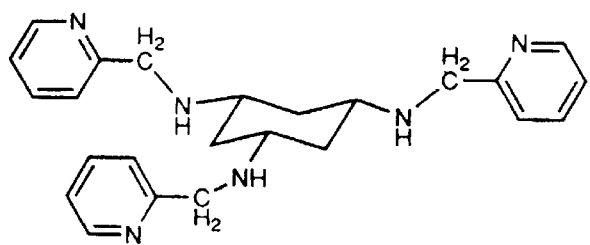
FIG. 1 illustrates the structure of known iron chelators such as tachpyr (shown in both the open and closed conformation), desferrioxamine (DFO), and PIH.
Figure 1:
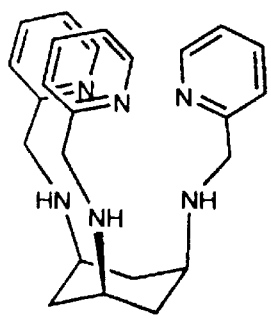
Figure 1:
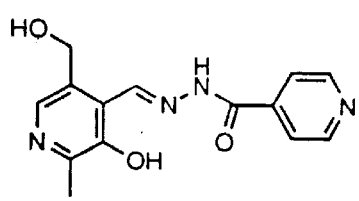
Figure 1:
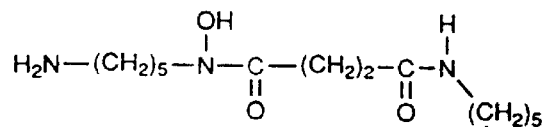
Figure 1:
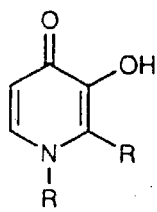
Figure 1:
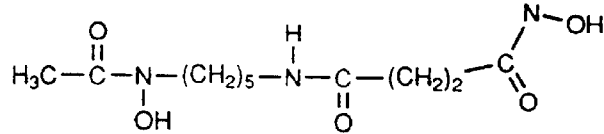
Figure 1:
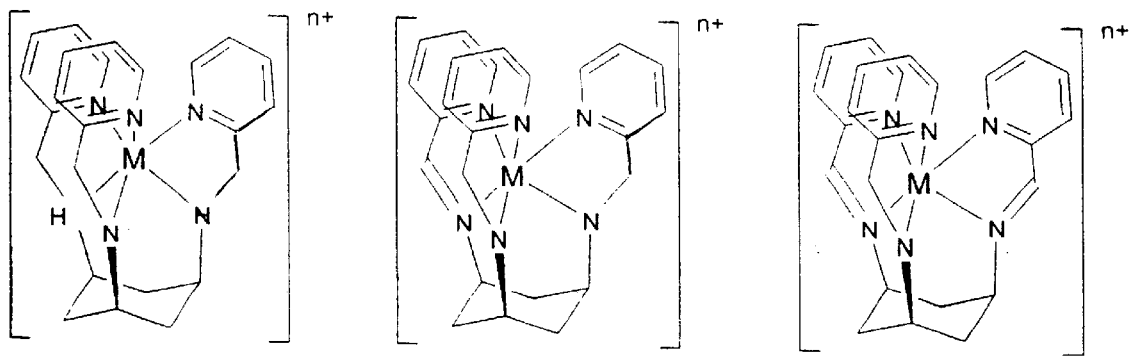
Figure 2:
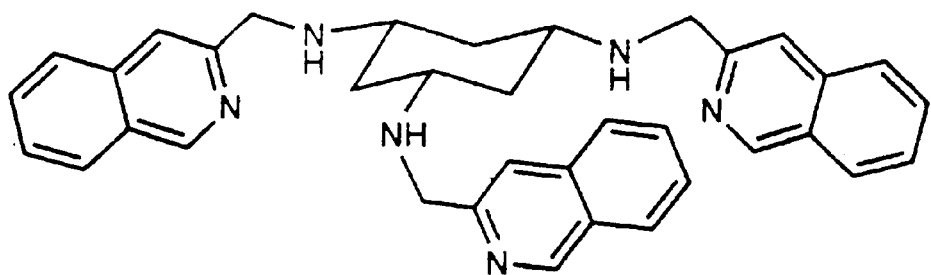
FIGS. 2 through 5 illustrate examples of the metal chelators in the present invention.
Figure 2:
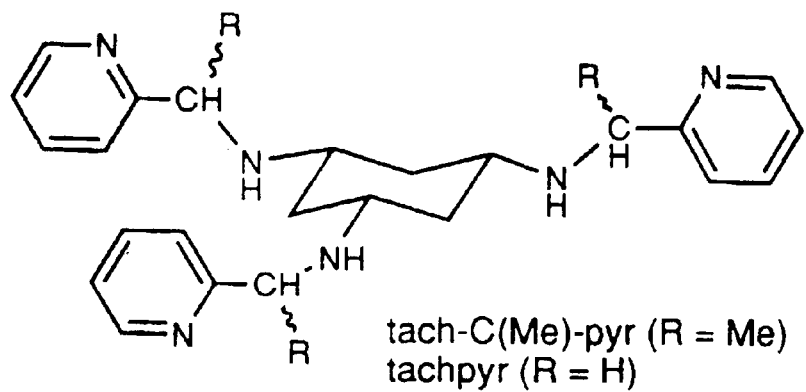
Figure 2:
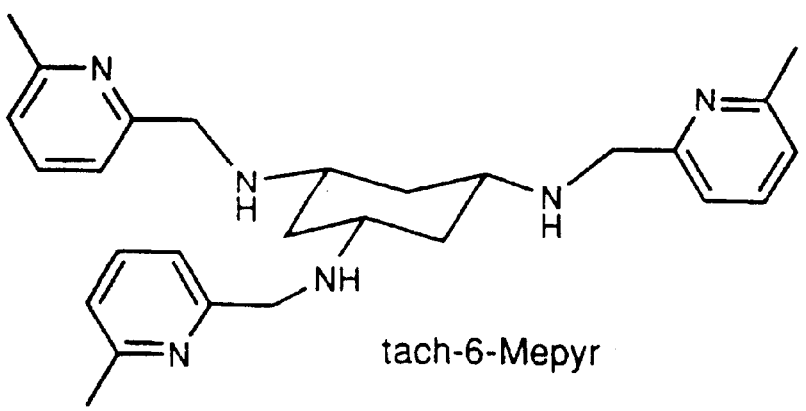

A novel family of hexadentate Fe(II) iron complexes and chelators based on cis, cis-1,3,5-triaminocyclohexane has been synthesized, which exhibits antiproliferative activity against tumor cells. The metal chelators and complexes of the present invention are represented by the general formula below:

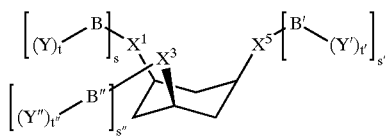

wherein:
- $X^1$, $X^3$, and $X^5$ are N, O or S, such at the $X^1$, $X^3$, and $X^5$ atoms are at the 1, 3, and 5 positions of a cyclohexyl group and are in a cis, cis disposition;
- B, B', and B" are aliphatic, branched aliphatic, or aryl groups, or any combination thereof, wherein the number of atoms between X and Y is about 2 to about 4;
- Y, Y' and Y" contain N, O, or S atoms that originate from either aliphatic, branched aliphatic, aryl, or heterocyclic groups, or a combination thereof, and/or Y, Y' and Y" are $NH_2$ or NHR, OH, or SH, $CO_2H$, $P(O)(OH)_2$, RP(O)OH, ROP(O)OH groups or a combination thereof, and R is H, aliphatic, branched aliphatic, or aryl groups, or a combination thereof that may or may not be identical in Y, Y' and Y";
- s, s', and s" are 0 to about 2; and
- t, t', and t" are 0 to about 2.

The chelators of the present invention include, but are not limited to, tachquin, tach-C(Me)-pyr, tach-6-Mepyr, S,S,S-tachen-2-Bn (also called tachbn), S,S,S-tachen-2-Me (also called tachpn), tachen-OH, tachcarbox, $(N—R)_3$tachpyr where R=Me Et, tachen-R, tach-N-Me-Im-imine, tachimpyr, tachpyr-$H_2$, and tachpyr-$2H_2$. Examples of these chelators are illustrated in FIGS. 2–5. The present chelators may be expected to chelate the biologically important metals Fe, Cu, Ni, Zn, Mn, Ca, and Mg as well as Ga, In, Cd, and Hg.

The combination of chemical features of the metal chelators of the present invention distinguishes them from known chelators that have been found to be cytotoxic. These features include: a) the cyclohexyl group framework; b) the chemical binding preference for Fe(II) over Fe(III); c) the ability to reductively capture Fe(III), particularly Fe(III) bound to biologically important molecules; d) the ability to form a modified chelator structure that has high affinity for Fe(II) through their reaction with Fe(III)-containing molecules; as well as e) the ability to form hydroxyl radical from hydrogen peroxide.

When added to MBT2 or T24 cultured bladder cancer-cells, tachpyr exhibited profound cytotoxicity toward cultured bladder tumor cells at concentrations approximately 8 $\mu$M or less. In fact, $IC_{50}$ values for MBT2 cells in four independent experiments were 4.6±2.0 $\mu$M as compared to 70 $\mu$M for desferrioxamine. Several iron complexes of this chelate were found to be nontoxic, suggesting that tachpyr exerts its cytotoxic effect through metal complexation. In further support of this theory, methyl and ethyl derivatives of tachpyr that are sterically hindered from complexing metals were not cytotoxic. Further, lipophilicity calculations yielded a partition coefficient (log $P_{OCT}$) of –0.10 for tachpyr, suggesting that tachpyr has the potential to function as an intracellular chelator.

The cytotoxicity of tachpyr towards bladder cancer cells is believed to involve coordination and targeting of intracellular iron. The toxicities of these chelators, eg tachen-Me, formerly termed tachpn, correspond to their ability to coordinate Fe(III) by reduction to Fe(II). Experiments show that these chelators remove Fe(III) from the biologically important form, Fe(III)(ATP)$_3$. The anaerobic reaction of tachpyr with Fe(II) salts affords the Fe(II)-tachpyr$^{2+}$ complex, but in the presence of oxygen, oxidative dehydrogenation of one or two of the aminomethylene group(s) of the ligand occurs, with formal loss of $H_2$: R—N(H)—C(H)$_2$-(2-py)→R—N=C(H)-(2-py)+$H_2$. The resulting mono- and dilmino Fe(II) complexes (denoted as [Fe(tachpyr-$H_2$)]$^{2+}$ and [Fe(tachpyr-$2H_2$)]$^{2+}$) are in inseparable mixture, but they may be fully oxidized by $H_2O_2$ to the known tris(imino) complex Fe(II)[cis,cis-1,3,5-tris(pyridine-2-carboxaldimino) cyclohexane]$^{2+}$ (or [Fe(tachpyr-$3H_2$)]$^{2+}$).

Cyclic voltammery of the imino complex mixture reveals an irreversible anodic wave at +0.78 V vs NHE. Fe-tachpyr complexes act as reducing agents toward $H_2O_2$, producing hydroxyl radical, a substance that is cytotoxic.

Tachpyr acts as a reducing agent toward Fe(III) salts, affording the same two Fe(II) imino complexes as products. Tachpyr also reductively removes Fe(III) from an Fe(II) (ATP)$_3$ complex (which is a putative form of intracellular iron), producing the two Fe(II) imino complexes. Novel N-alkylated derivatives of tachpyr have been synthesized. N-alkylation has two effects on tachpyr: lowering metal affinity through increased steric hindrance, and preventing Fe(III) reduction because oxidative dehydrogenation of nitrogen is blocked. The N-methyl tachpyr derivative binds Fe(II) only weakly as a high-spin complex, and no complexation or reduction of Fe(III) is observed. Corresponding to their inability to bind iron, the N-alkylated chelators are nontoxic to cultured bladder cancer cells. A tach-based chelator with three N-propyleneamino arms was also synthesized. Studies of the chemical and biochemical properties of this chelator further supports a relationship between intracellular iron chelation, iron reduction, and cytotoxicity. Thus, this chelator exhibits both a decrease in the ability to undergo oxidative dehydrogenation and cytotoxicity when compared to tachpyr.

The data strongly imply that the chelator derivatives have potential application to cancer therapy as chemotherapeutic agents and any other diseases where affecting iron metabolism may be relevant, including but not limited to, any iron overload conditions, vasospasm, Parkinson's disease and malaria.

The metal chelators may be in various forms including chemical compounds comprising varying numbers of chelating moieties linked by a linking group, wherein each chelating moiety is linear or a cyclic hydrocarbon substituted at one or more positions by a donor atom selected from the group consisting of nitrogen, oxygen and sulfur, wherein the linking group is a hydrocarbon backbone substituted by one or more donor atoms from the group consisting of nitrogen, oxygen, and sulfur.

The linking group of the present invention may vary. Preferably, the linking group is a hydrocarbon molecule substituted at one or more carbons by a donor atom selected from the group consisting of —N—, —O—, and —S—. Preferably, the linking group is substituted by nitrogen. In one embodiment of the present invention, the linking group is substituted by three nitrogens. Of particular interest is cis,cis-1,3,5-triaminocyclohexane.

The chelating moieties of the compound vary in number, and may be identical or different. In one embodiment of the present invention, the compound comprises three identical rings. The chelating moiety is substituted in one or more positions with a donor atom selected from the group consisting of —N—, —O—, and —S. Preferably, the chelating moiety is a carbon ring substituted by nitrogen. In one embodiment of the present invention, the compound comprises a linking group attached to a varying number of 2-pyridyl methyl pendant arms. The ring can be substituted by a donor atom in any position other than the point of linkage to the linking group. The rings can be further substituted, provided that substitution does not sterically interfere with the binding of the metal ion.

The chelating moieties are attached to the linking group in a manner designed to orient the donor atoms of the compound in a position suitable to bind a metal ion. In one embodiment of the present invention, a ring is attached to a linking group through the linking group donor atom. In a further embodiment of the present invention, the compound comprises cis-1,3,5 triaminocyclohexane with a $CH_2CH(R)NH_2$ pendant arm on each nitrogen, where R is an aromatic or aliphatic group.

A preferred embodiment of the metal chelators of the present invention is represented by the following chemical formula:

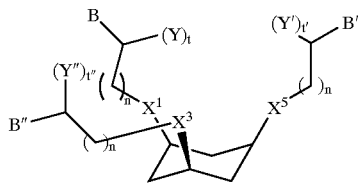

wherein:
$X^1$, $X^3$, and $X^5$ are N, O or S, such at the $X^1$, $X^3$, and $X^5$ atoms are at the 1, 3, and 5 positions of a cyclohexyl group and are in a cis, cis disposition;

B, B', and B" are aliphatic, branched aliphatic, or aryl groups, or any combination thereof, wherein the number of atoms between X and Y is about 2 to about 4;

Y, Y' and Y" contain N, O, or S atoms that originate from either aliphatic, branched aliphatic, aryl, or heterocyclic groups, or any combination thereof, or $NH_2$ or NHR, OH, or SH, $CO_2H$, $P(O)(OH)_2$, $RP(O)OH$, $ROP(O)OH$ groups or any combination thereof, and R is H, aliphatic, branched aliphatic, or aryl groups, or any combination thereof that may or may not be identical in Y, Y' and Y";

t, t', and t" are 0 to about 2; and n is between 0 and about 3.

In yet another preferred embodiment, the metal chelators of the present invention arer represented by the chemical formula:

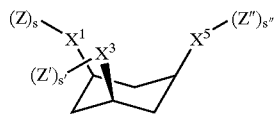

wherein:
$X^1$, $X^3$, and $X^5$ are N, O or S, such at the $X^1$, $X^3$, and $X^5$ atoms are at the 1, 3, and 5 positions of a cyclohexyl group and are in a cis, cis disposition; and s, s', s" are 0 to about 2;

and Z, Z', Z" = 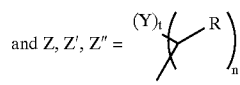

wherein:
R is H, aliphatic, branched aliphatic, or aryl groups, or any combination thereof that may or may not be identical in Z, Z' and Z";

Y is $NH_2$ or NHR', OH, or SH, $CO_2H$, $P(O)(OH)_2$, $RP(O)OH$, $R'OP(O)OH$ groups, or a combination of these is R' is H, aliphatic, branched aliphatic, or aryl groups, or any combination thereof, or Y is a group containing N, O, or S atoms that originate from either aliphatic, branched aliphatic, aryl, heterocyclic groups, or any combination thereof, in any case, Y and R' may or may not be identical in Z, Z' and Z";

t is 0 to about 2;

n is between 0 and about 3.

The composition of the present invention binds or chelates metal ions with coordinates equal to or less than the total number of chelating moieties of the present invention. Preferably, the present composition binds metal ions of six coordinates, or hexadentate ions, although the composition can be designed to accommodate metal ions of greater than six coordinates. In one embodiment, the present composition binds Fe(III). In a further embodiment, the present composition binds Fe(II).

The ability of the composition of the present invention to penetrate cell membranes is a useful feature of the present invention. Compositions that translocate the cell membrane are available to chelate intracellular iron pools. Preferred compounds are,thus, lipophilitic. In one embodiment, the compound has a partition coefficient of –0.10 $\log_{oct}$.

The compositions of the present invention can be formulated for use as pharmaceuticals including chemotherapeutic agents. When the metal chelators are used in accordance with the present invention, they can be formulated into the desired dosage forms such as capsules, tablets, powders, suspensions, emulsions, solutions, syrups, aerosols, soft and hard gelatin capsules, suppositories, injectable solutions and the like. The metal chelators can be administered by itself or in combination with pharmaceutically acceptable carriers, diluents, stabilizers, solubilizers, lubricants, binders and the like or excipients thereof.

While all of these various modes of administration are contemplated, oral administration is the preferred route of administration. The compositions can be orally administered by incorporating them with a liquid diluant or a solid carrier. As a pharmaceutical, the composition of the present invention can be used to reduce the level of iron in cells in need of such a reduction. In one embodiment, the composition of the present invention is used to inhibit tumor cell growth. While the composition of the present invention is used in the therapeutic reduction of iron, the composition may also be used to remove other metals present in amounts in need of reduction.

In the detailed description of the present invention below, Example 1 generally describes the materials used to carry out the synthesis of the metal chelators of the present invention.

Example 2 describes the synthesis of a prototype chelator and its alkylated derivatives. More specifically, Example 2 describes the synthesis of a hexadentate chelator known as tachpyr characterized by the addition of a 2-pyridylmethyl pendant arm to each secondary amine of a triamino linking group. Example 2 also describes the synthesis of tachpyr's alkylated derivates, where the secondary amines are further substituted by methyl or ethyl groups.

Example 3 describes the preparation of metal complexes of tachpyr. Metal complexes prepared include M[tachpyr][X]2," wherein M is Fe(II),Ca(II), Mg(II), or Cu(II) and X is Cl—; and wherein M is Mn(II) or Zn(II) and X is $ClO_4$—; $M=Ga^{3+}$, $X=NO_3$.

Example 4 describes the preparation of hexadentate, low-spin, cationic metal complexes produced from the interaction of Fe(II) and Fe(III) with the Fe(II) chelators, tachpyr and tach-C(Me)pyr, particurlarly the differences in the behavior of the two chelators.

Example 5 describes the preparation of ligands.

Example 6 describes the electrochemical studies that were conducted on the metal complexes and the ability of Fe-tachpyr complexes to produce hydroxyl radical.

Example 7 describes the reaction of Fe(III)-ATP (1:3) complex with tachpyr.

Example 8 describes the effect of tachpyr upon the viability of various types of tumor and normal cells.

Examples 9 and 10 examine the ability of tachpyr to chelate intracellular iron. Example 9 examines the effect of tachpyr on ferritin synthesis, which is regulated by intracellular iron levels. Example 10 examines the partition coefficient of tachpyr as evidence of the chelator's ability to penetrate the cell membrane and access intracellular iron pools.

Examples 11, 12, and 13 examine the metal ion specificity of tachpyr. More particularly, Example 11 describes the cytotoxicity of the chelator relative to its various chelates, including Fe(II), Mg(II), Mn(II); Cu(II), Zn(II), and Ga(III). Example 12 describes the effect of alkylation on the ability of tachpyr to bind a metal ion. Example 13 describes the effect of alkylation on bond length by examining the single-crystal x ray structure of alkylated and non-alkylated tachpyr.

Example 14 describes apoptosis with tachpyr.

The chelators of the present invention were prepared in accordance with the following methods.

Figure 6:
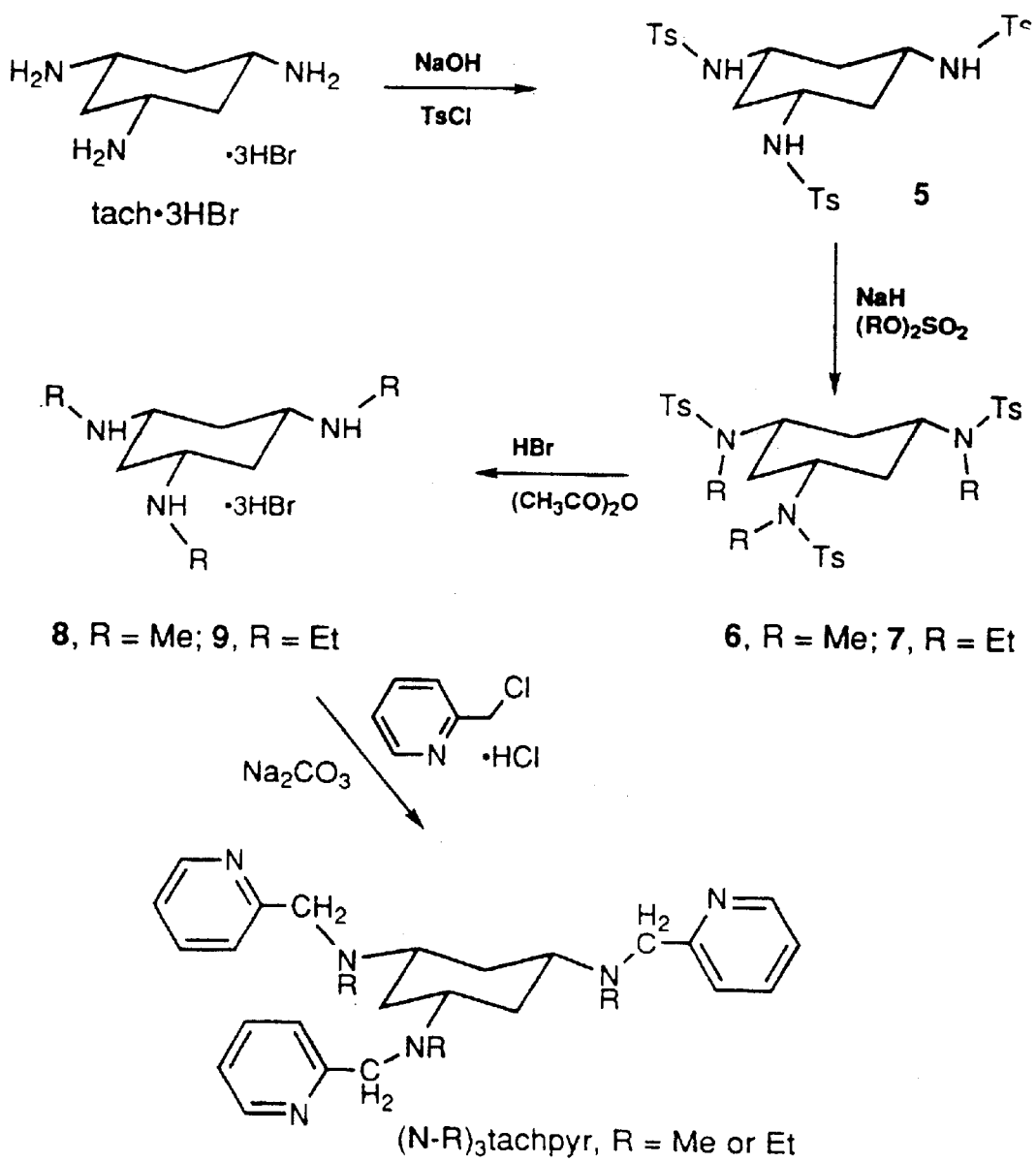
FIG. 6 illustrates a method for the modification of tachpyr to increase steric hindrance and blocking of N—H activation: syntheses of (N—R)$_3$tachpyr (R=Me, Et)

Modification of tachpyr for increased steric hindrance and blocking of N—H activation: syntheses of (N—R)$_3$tachpyr (R=Me, Et) may be accomplished utilizing the scheme shown in FIG. 6 (Scheme 3). The N-alkylation of tach employing p-toluenesulfonamide protection of nitrogen is adapted from the literature [Paul-Roth, C. et al., *Inorg. Chem.* 34:1408–1412 (1995)]. The N,N',N''-tritosylamide derivative of tach (5) is obtained from tach and TsCl. The tosylamide 5 is deprotonated with NaH, quenching the anion with dialkylsulfate as a source of the methyl or ethyl group to afford 6 or 7. The tosylates were then efficiently removed with HBr in acetic anhydride to provide the desired product triamine 8 or 9 in good yield. The N,N',N''-trialkyl-N,N',N''-tris(2-pyridylmethyl) derivatives of tach are prepared by alkylation of the appropriate triamine 8 or 9 with 2-chloromethylpyridine hydrochloride in dry DMF with excess base. The pure product is isolated by column chromatography on silica gel.

Figure 7:
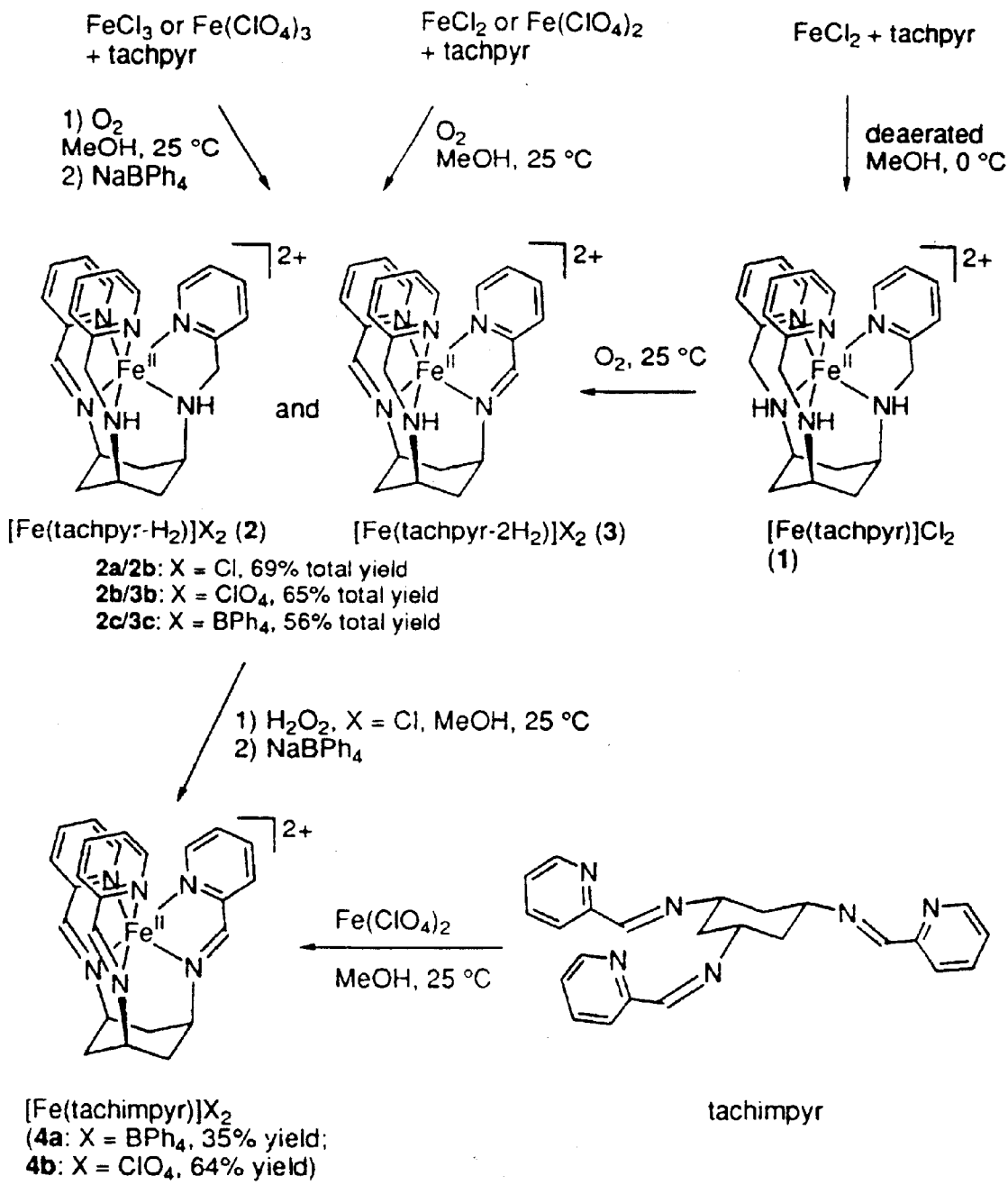
FIG. 7 and FIG. 7A illustrate metal complexation by the chelators of the present invention.
Figure 7A:
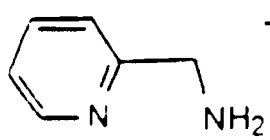
Figure 7A:
Figure 7A:
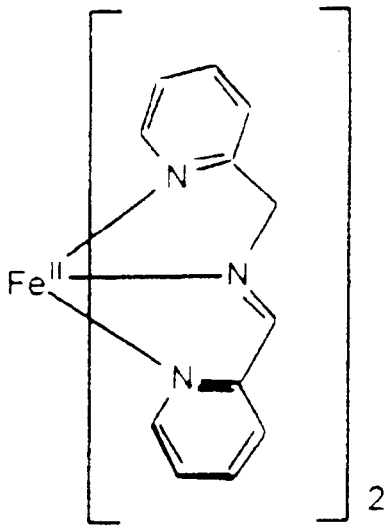
Figure 7A:
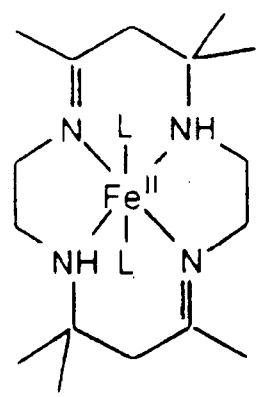
Figure 7A:
Figure 7A:
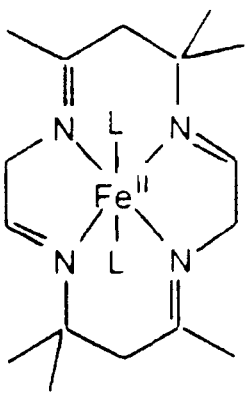
Figure 7A:

Metal complexation by the chelators of the present invention is depicted in FIG. 7. As shown in FIG. 7, it is observed that the reaction of Fe(II) with tachpyr at 0° C. in MeOH with exclusion of O$_2$, affords [Fe(tachpyr)]Cl$_2$ (1), the initial complex between Fe(II) and tachpyr prior to oxidation. Iron(II) chloride or perchlorate salts react with tachpyr in the presence of oxygen, affording an inseparable mixture of products, 2 and 3, in which tachpyr has been oxidatively dehydrogenated. In 2 or 3, one or two of the three secondary amine donors of tachpyr are replaced by imine donors. This is in analogy to the reaction of iron with 2-aminomethylpyridine (ampy) which is believed to give the corresponding imine complex initially, followed by hydrolysis and condensation (Scheme 2a) as shown in FIG. 7A [Chum, H. L. et al., *Inorg. Chem.* 21:1146 (1982) and Holanda, MID et al., *Inorg. Chem.* 15:890–93 (1976)].

The assignment of products is based on elemental analysis, UV-visible spectroscopy, and partial assignment of the $^1$H NMR spectra, as well as on subsequent reaction chemistry (vide infra). UV-visible spectra of the mixture of 2 and 3 indicate two absorbances at 602 nm (e=1710) and 412 nm (e=5000), which are assigned as charge-transfer peaks[Goedken, V. L. et al., *J. Am. Chem. Soc.* 94:7355 (1972)]. The $^1$H NMR spectrum of the mixture of 2 and 3 is complex due to the lack of a mirror plane of symmetry in either molecule, which arises presumably from the twist of the arms of tach chelator complexes such as we have previously observed in the X-ray structure of Ga(tachpyr) (NO$_3$)$_3$. [Hilfiker, K. A. et al., *Inorg. Chem.* 36:4600–03 (1997)]. However, the imine region clearly indicates a single peak (9.51 d in DMSO-d$_6$) assigned to the imine C—H of 2 and two peaks (8.32 and 8.21 d in DMSO-d$_6$) assigned to the two imine C—H's of 3. Goedken and Busch [*Am. Chem. Soc.* 94:7355 (1972)] obtained the complex [Fe([14]dieneN$_4$)—(CH$_3$CN)$_2$][ClO$_4$]$_2$ (see Scheme 2b in FIG. 7A) analogous to our 1 from reaction of Fe(II) and the diamine-diimine ligand Me$_6$[14]4,11-dieneN$_4$. They observed stepwise oxidations (all by O$_2$) of [Fe([14]dieneN$_4$)—(CH$_3$CN)$_2$][ClO$_4$]$_2$ to the corresponding Fe(III) complex followed by oxidative dehydrogenation to a monoamine-triimino complex and finally a tetraimino complex of Fe(II).

Upon completing the oxidation of 2a and 3a with H$_2$O$_2$ followed by anion exchange to precipitate a solid, the triimino complex [Fe(tachimpy)][BPh$_4$]$_2$ (4a) can be isolated. This complex shows proton NMR data that are very similar to that of [Fe(tachimpy)] [ClO$_4$]$_2$, which was first prepared directly from pyridine-2-carboxaldehyde, tach, FeSO$_4$ and HClO$_4$ by Lions and Martin [*Am. Chem. Soc.* 79:1572–75 (1957)].

A preliminary study of the redox behavior of a mixture of 2a and 3a by rotating ring disc electrode cyclic voltammetry techniques reveals an anodic wave at ca. 0.78 V vs. NHE which we ascribe to formation of 4 by the oxidation of 2 and/or 3 (FIG. 7). There is evidence that this process is diffusion-limited, as determined by variation of the rotation speed of the working electrode. No cathodic current corresponding to a reverse process was observed. In an attempt to study the kinetics and intermediates of a possible reverse process, the ring was maintained at a reducing potential (0.44 V vs. NHE) while the disc electrod was swept through the anodic potential. No current was detected.

The cytotoxicity of the metal chelators of the present invention is described as follows. Corresponding to the observations that Fe(II) and Fe(III) interact strongly with tachpyr, this chelator was found to be extremely toxic to cultures of human and mouse bladder tumor cells, while the (N—R)$_3$tachpyr (R=Me, Et) chelators were essentially non-toxic. Further, there is strong evidence that treatment with tachpyr induces a state of cellular iron deprivation.

All complexation studies indicate that (N-Me)$_3$tachpyr is a less effective chelator of iron than tachpyr. The interaction of (N-Me)$_3$tachpyr with Fe(ClO$_4$)$_2$.6H$_2$O in dry MeOH affords a paramagnetic, pale-green powder (10). Based on elemental analyses and mass spectra, this composition was tentatively asssigned the high-spin Fe(II) complex Fe[(N-Me)$_3$tachpyr][ClO$_4$]$_2$. While 1–4 are low-spin complexes, the spin state of 10 indicates that the metal-ligand interaction is weak, which we ascribe to the steric effects of the N-alkyl groups. The steric effects of N-alkylation of tachpyr on X-ray structural parameters of metal complexes, which includes the lengthening of metal-nitrogen bonds.

The interaction of Fe(ClO$_4$)$_3$.6H$_2$O with (N-Me)$_3$tachpyr leads to an oily material (11) whose proton NMR signals are slightly broader and shifted relative to those of the free ligand. The perturbation of the ligand signals is attributed to a weak interaction of high-spin Fe(III) with the ligand, which induces a contact shift [see Drago, R. S., Physical Methods for Chemists. Saunders, pp 519 (1992)] in the $^1$H NMR spectrum of (N-Me)$_3$tachpyr. In the case of Fe(III), the inability of (N-Me)$_3$tachpyr to strongly complex Fe(both III) is attributed to steric effects (which are greater for Fe(III) than Fe(II) due to the smaller size of Fe(III)) and to the inability of (N-Me)$_3$tachpyr to form an imine and to thereby reduce Fe(III).

Fe(III) is reduced to Fe(II) by tachpyr and tach-C(Me)pyr, a process that may be relevant to the biological action of tachpyr because a large portion of cellular iron exists as Fe(III) (see below). Reaction of Fe(III) (Cl$^-$ or ClO$_4^-$ salts) with tachpyr leads to the mixture of 2 and 3, isolated as BPh$_4^-$ salts. It is not known whether an intermediate complex of Fe(III) with tachpyr exists, in analogy to the Fe(II) complex 1 which has been isolated. Tach-C(Me)pyr has a greater propensity to form reduction products with Fe than does tachpyr.

Tachpyr reacts with the 1:3 complex of Fe(III) with ATP [Mansour, A. N. et al, *J. Biol. Chem.* 260:7975:79 (1985)] to afford 2 and 3. Membrane-permeable chelators are believed to complex intracellular iron that exists in an incompletely characterized state known as the intracellular labile iron pool, [Breuer, W. et al., *J. Biol. Chem.* 270:24209–15 (1995)] in a fashion that is believed to yield either Fe(II) or Fe(III)-ligand complexes. Because Fe(III) is reduced to Fe(II) in its reaction with tachpyr, we suggest the possibility of complexation and reduction of Fe(III) from postulated cytoplasmic sources such as Fe(III)-ATP as a new mode of toxicity of iron chelators.

A weakly toxic tach chelator whose oxidative dehydrogenation process may be sterically hindered is exemplified by (N—R)$_3$-tachpyr. The mechanism of oxidative dehydrogenation has been the subject of a number of studies with differing opinions on the rate determining step [Goto, M. et al., *J. Chem. Soc, Chem.* Commun. 2015–2016 (1994) and Keene, F. R., et al., *J. Am. Chem. Soc.* 105:7075–81 (1983)]. Regardless of the outcome, it is apparent that steric and electronic effects on H$^\alpha$ are important in the process.

Figure 3:
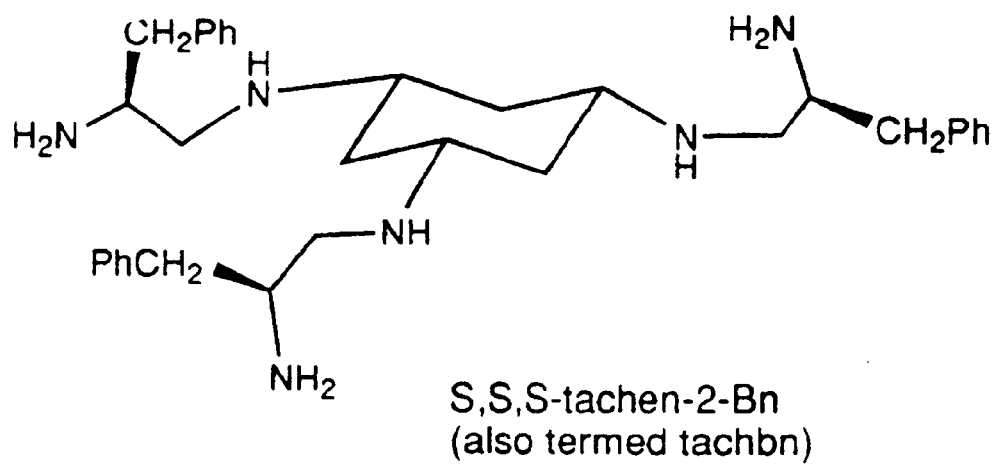
Figure 3:
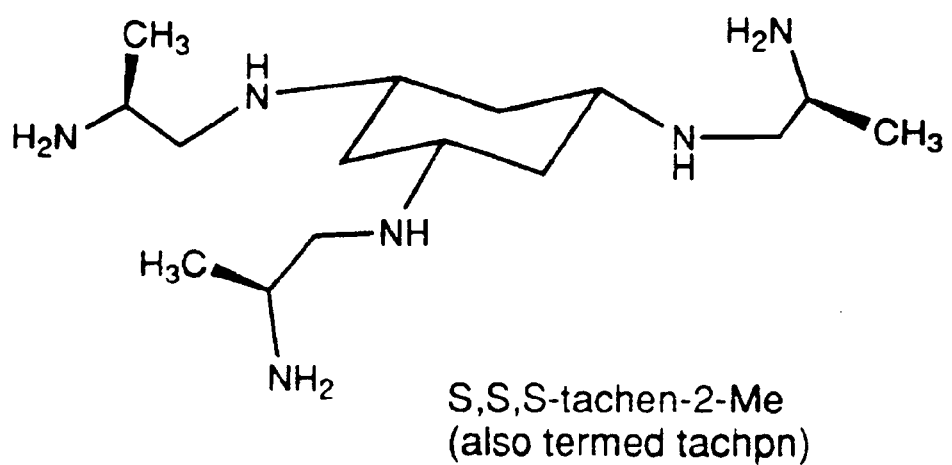

In order to further explore the hypothesis that oxidative dehydrogenation is involved in chelator toxicity, the tach-based chelator with three N-propyleneamino arms (termed tachpn, Scheme 4 as shown in FIG. 3) has been studied. Tachpn is distinguished from tachpyr in having the —C(H)(CH$_3$)(NH$_2$) fragment in place of the pyridine ring. The α-hydrogens of tachpn are sterically hindered, relative to tachpyr, by the methyl group in the β position, so that tachpn may have a lower propensity toward α-hydrogen abstraction. Further, the pseudo-benzylic H$^\alpha$ of tachpyr would also have a potentially greater tendency to be abstracted, as compared to tachpn, on electronic grounds [see March, J., *Advanced Organic Chemistry.* McGraw-Hill, pp 914 ff) The considerations would imply that tachpn is less able than tachpyr to undergo oxidative dehydrogenation and to reduce Fe(III). Preliminary cell culture experiments were conducted to compare the toxicity of tachpyr with tachpn (FIG. 3). These tests show the IC$_{50}$ value of tachpn to be approximately 80 μM, a 17-fold decrease in toxicity relative to tachpyr.

The following Examples further illustrate the present invention.

EXAMPLE 1

Materials

Anhydrous grade MeOH was obtained from Fisher. Et$_2$O was distilled from Na/K. Anhydrous grade DMSO and DMF were obtained from Aldrich. Other chemicals were purchased from Aldrich, Sigma or Fluka and used as received.

Proton and $^{13}$C NMR were obtained at 300 MHz with a Gemini 300XL instrument or at 360 MHz with a Bruker AM360 instrument. Chemical shifts are reported in ppm on the "d" scale relative to TMS (DMSO or CDCl$_3$ solutions), or TSP (D$_2$O solutions). Proton chemical shifts are annotated as follows: ppm (multiplicity or spin system, coupling constant if measurable, integral, assignment). Chemical ionization mass spectra (CI-MS) were obtained on a Finnegan 3000 instrument. Fast atom bombardment (FAB-MS) mass spectra in the positive ion detection mode were obtained on an Extrel 400 instrument. Elemental analyses were performed by the University of NH Instrumentation Center, Atlantic Microlabs (Atlanta, Ga.) or Galbraith Laboratories (Knoxville, Tenn.) UV-Vis spectra were measured on an HP 8453 diode-array spectrometer. HPLC analyses were conducted with a Waters 600E/486/746 dual-pump system with UV detection at 254 nm. A Beckman Ultrasphere 4.6×25 cm RP-18 column was eluted with a gradient of 100% 0.05 M Et$_3$NHOAc to 100% MeOH over 24 min. A computer-interfaced scanning bipotentiostat (Pine Instrument Co., model AFCBP1) was employed for cyclic voltammetry. The working electrode was a Pt-rotating ring disk electrode (RRDE) at 1600 RPM (Pine Instrument Co.), with a SCE reference electrode and a glassy carbon counterelectrode.

EXAMPLE 2

Preparation of Tachpyr and its Alkylated Derivatives

Figure 4:
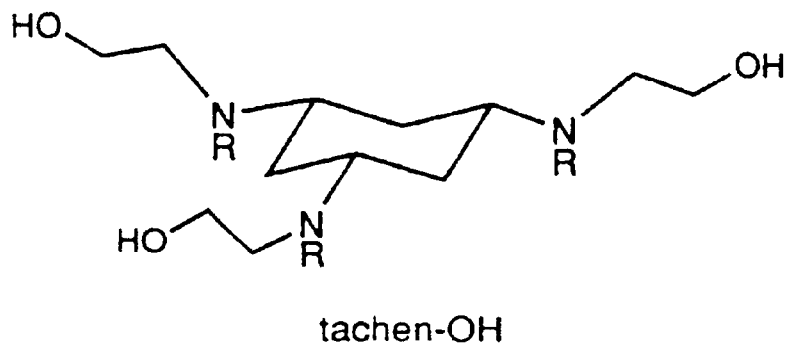
Figure 4:
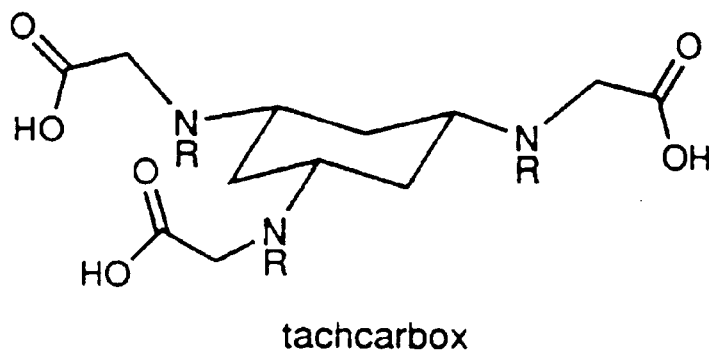
Figure 4:
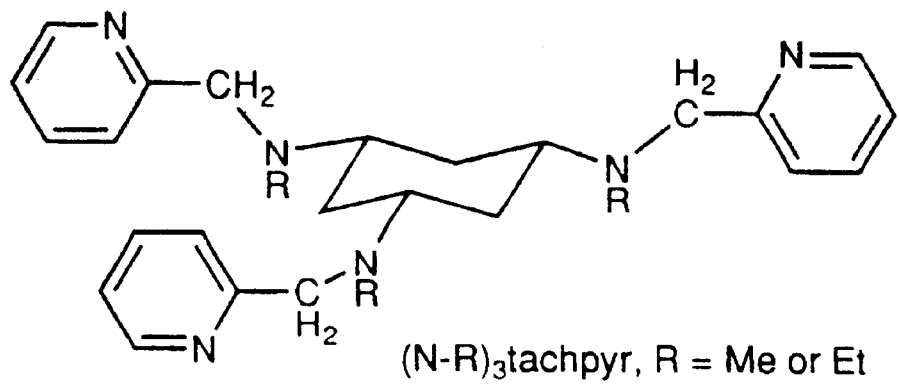
Figure 5:
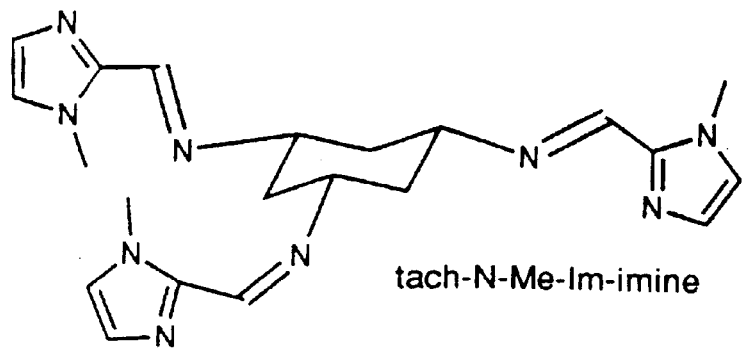
Figure 5:
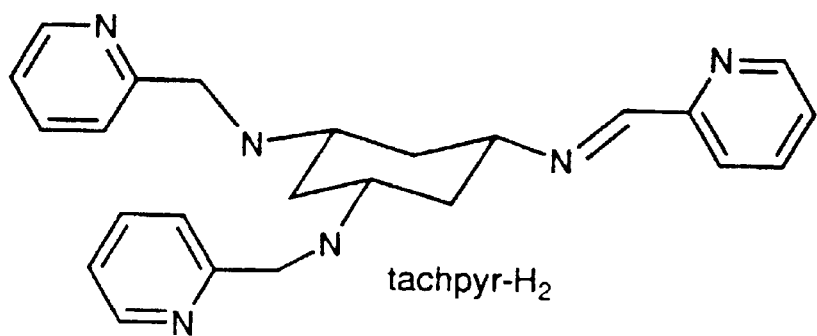
Figure 5:
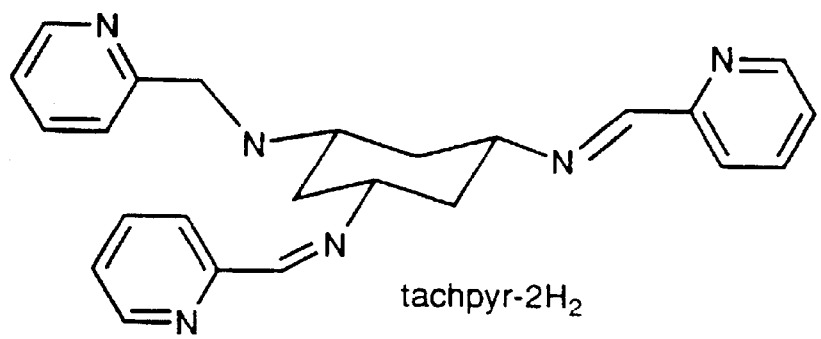

A hexadentate chelator (tachpyr) was synthesized from the triamine cis-1,3,5-triaminocyclohexane (tach) by the addition of a 2-pyridylmethyl pendant arm on each nitrogen in accordance with the procedure disclosed in Bowen, T. et al., *Bioorg. Med. Chem. Lett.* 6:807 (1996). FIG. 1 illustrates the structure of tachpyr in both the open and closed conformations. Alkylated derivatives of tachpyr were synthesized, including (N-Me)$_3$tachpyr and (N—Et)$_3$tachpyr, and N-alkylated derivatives. FIG. 4 illustrates the structure of alkylated derivatives of tachpyr (see (N—R)$_3$tachpyr, R=Me or Et).

To purify and facilitate handling of the chelators, their nitrate salts were prepared by treating the chelators with excess nitric acid in ethanol. Typically, 8 molar equivalents of concentrated nitric acid were added to a solution of 5×10$^{-3}$ mol of tachpyr in 1 mL of anhydrous ethanol. The pale green precipitate was washed twice with 8 ml of anhydrous diethyl ether and dried under reduced pressure (5×10$^{-2}$ Torr). The nitrate salts were determined by elemental analysis to be tachpyr, (HNO$_3$)$_5$, (N-Me)$_3$tachpyr (HNO$_3$)$_6$ and (N—Et)$_3$tachpyr(HNO$_3$)$_6$.

EXAMPLE 3

Preparation of Metal Complexes of Tachpyr

Metal complexes of tachpyr were prepared by a reaction of the appropriate metal salt with the chelator in a methanol solution, followed by slow diffusion of diethyl ether into the reaction solution. Recrystallization was then conducted to achieve sufficient purity, which was determined by combustion analyses. Compounds were dissolved in phosphate buffered saline, pH 7.4, before use in cytotoxicity assays. Metal complexes which were prepared include: "M[tachpyr][X]2," wherein M is Fe(II), Ca(II), Mg(II), Cu(II) and X is Cl$^-$; and wherein M is Mn(II), Zn(II) and X is ClO$_4$—; M is Ga$^{3+}$ X is NO$_3$. FIG. 1 illustrates the structure of the metal complexes of tachpyr.

EXAMPLE 4

Preparation of Iron Complexes of Tachpyr and Tach-C(Me)pyr

A. Preparation of [Fe(tachpyr)]Cl$_2$ (1)

A pale green solution of FeCl$_2$.4H$_2$O (0.0229 g, 1.15×10$^4$ mol) in methanol (2 mL) was degassed in a Schlenk flask by purging with N$_2$ for 5 min. A similarly degassed yellow solution of tachpyr (0.0464 g, 1.15×10$^4$ mol) in methanol (2 mL) was added. The mixture attained a brown color while stirring for 30 min at 0° C. under N$_2$. Layering with Et$_2$O produced a brown precipitate that was isolated by filtration under N$_2$, dried under reduced pressure, and stored under N$_2$ in a Schlenk flask. $^1$H NMR (DMSO-d$_6$, 360 MHz, 25° C.): d 7.80, 7.58, 7.26, 6.98 (t, d, t, d, 4H, C$_5$H$_4$N); 5.55 (t, 1H, NH); 4.43, 4.10 (ABX, 2H, py-CH$_2$); 3.07 (s, 1H, cyclohexyl methine H); 2.09, 1.86 (AB,J=14.8 Hz, 2H, cyclohexyl methylene H's, diastereotopic). Air-sensitivity of the product interfered with further characterization.

B. Conversion of 1 to a Mixture of 2a and 3a

Complex 1 (solid) was exposed to air for 1 hour at 25° C. A color change from brown to green-brown occurred. The product was identified as a mixture of 2a and 3a by $^1$H NMR spectroscopy.

C. Preparation of a Mixture of [Fe(tachpyr-H$_2$)]Cl$_2$ (2a) and [Fe(tachpyr-2H$_2$)]Cl$_2$ (3a) from FeCl$_2$.4H$_2$O and Tachpyr; Preparation of Fe(tach-C(Me)pyr-nH$_2$)$^{2+}$ (n=1,2)

To a pale green solution of FeCl$_2$ (0.0179 g, 9.01×10$^{-5}$ mol) in methanol (2 mL) was added a yellow solution of tachpyr (0.036 g, 9.01×10$^{-5}$ mol) in methanol (2 mL) affording a dark brown-green solution. After standing for 0.5 h, ether (12 mL) was layered into the mixture to form a dark green precipitate and a green solution. The precipitate was isolated by decantation and dried under reduced pressure affording the product in 69.3% yield (0.0149 g, 2.82×10$^{-5}$ mol) as a dark brown-green solid. $^1$H NMR (DMSO-d6, 360 MHz, 25° C.); d 9.40, 9.38,9.30 (s, 3 imine H, RN=C(H)R'); numerous peaks from 8.5 d to 7.3 d for pyridine hydrogens; 4 peaks from 6.3 d to 5.5 d for (NH); 6 peaks from 5.0 d to 4.3 d for (py-CH$_2$); numerous peaks from 2.9 d to 4.3 d for (cyclohexyl methine H) and (cyclohexyl methylene H's).

D. Preparation of (Fe(tachimpy)][BPh$_4$]$_2$ (4a)

To a pale green solution of FeCl$_2$.4H$_2$O (0.0219 g, 1.10×10$^{-4}$ mol) in methanol (2 mL) was added a yellow solution of tachpyr (0.044 g, 1.10×10$^{-4}$ mol) in methanol (2 mL) affording a dark brown-green solution. Adding 4 drops of H$_2$O$_2$ (30%) gave a blue-purple solution that was let stand one hour and then layered with Et$_2$O (10 mL), forming a purple precipitate immediately. The purple precipitate was purified by decanting the supernatant, taking the solid up in acetone (5 mL), filtering, and drying under reduced pressure, then repeating the acetone extraction and drying process to give a purple solid. The solid was dissolved in methanol (2 mL), treated with NaBPh$_4$ (0.05 g in 2 mL of methanol) giving a purple precipitate which was isolated and dried under reduced pressure. This precipitate was extracted into acetone (5 mL), filtered and dried under reduced pressure. The solid was washed with CH$_2$Cl$_2$ (5 mL) and dried under reduced pressure affording the product in 35.5% yield (0.0301 g, 4.79×10$^{-5}$ mol) as a purple solid. $^1$H NMR (DMSO-d$_6$, 360 MHz, 25° C.): d 9.18 (s, 1H, N=CH-py) 8.38, 8.22, 7.59, 6.69 (d, t, t, d, 4H, C$_5$H$_4$N); 7.59, 6.90, 6.77( s, t, t, B(C$_6$H$_6$)$_4$); 4.79 (s, 1H, cyclohexyl methine H); 2.57, 1.79 (AB, J=14.6 Hz, 2H, cyclohexyl methylene H's, diastereotopic). UV (MeOH) 582 nm (e=5220), 328 nm (e=2950). Tach-C(Me)pyr forms the complex Fe[(tach-C(Me)pyr-3H$_2$]$^{2+}$ more readily than does tachpyr. Thus, the above procedure affords Fe[(tach-C(Me)pyr-3H$_2$]$^{2+}$ using O$_2$, not H$_2$O$_2$, in reaction of Fe(ClO$_4$)$_2$ with tach-C(Me)pyr.

E. Preparation of [Fe(N-Me)$_3$tachpyr](ClO$_4$)$_2$ (10)

To a pale yellow solution of Fe(ClO$_4$)$_2$.6H$_2$O (0.0374 g, 1.03×10$^{-4}$ mol) in methanol (2 mL) was added a pale yellow solution of (N-Me$_3$)tachpyr (0.0458g, 1.03×10$^{-4}$ mol) in methanol (2 mL) affording a brown-green solution. After standing for 3 hours, a grey-green microcrystalline material was deposited. The product was purified by decanting the supernatant and washing with Et$_2$O followed by drying under reduced pressure affording the product in 77.7% yield (0.0647 g, 9.27×10$^{-5}$ mol) as a green solid. Anal. Calcd for C$_{27}$H$_{38}$N$_6$Cl$_2$O$_9$ ([Fe(N-Me)$_3$tachpyr](ClO$_4$)$_2$.H$_2$O): C, 45.21; H, 5.34; N, 11.71. Found: C, 44.90; H, 5.08; N, 11.88. MS (FAB/DMSO/glycerol): 500 (M-2ClO$_4$$^-$).

EXAMPLE 5

Preparation of Ligands

A. Preparation of 1,3,5-cis,cis-Triaminocyclohexane-N,N',N"-tri-p-toluenesulfonyl Amide (5)

The salt tach.3HBr (7.6 g, 20.4 mmol) was dissolved in H$_2$O (25 mL) with NaOH (4.9 g, 120 mmol) to form a clear solution. Dioxane (150 mL) was added and the solution was cooled in an ice bath. In dioxane (75 mL),p-toluenesulfonyl chloride (11.69 g, 61.3 mmol) was added dropwise. The reaction was allowed to come to room temperature and then stirred for 18 h. The reaction solution was then extracted into EtOAc (250 mL), and after the layers separated, washed with salt solution (100 mL). After drying over Na$_2$SO$_4$ and filtration, the solvent was removed by rotary evaporation to leave a white solid. The product was isolated by column chromatography on silica with MeOH/CHCl$_3$ (5/95%) to leave, after removal of the solvents, a white solid. (11.0 g, 89%). Anal. Calcd. for C$_{27}$H$_{33}$N$_3$O$_6$S$_3$; C, 54.78; H, 5.63; N, 7.10. Found: C, 54.74, H, 5.59; N, 7.02 $^1$H NMR (d$_6$-DMSO) d 7.60–7.50 (m,3H), 7.34 (d,2H,J=7.8), 2.95 (m,1H), 2.40 (s,3H), 1.50 (br.d,1H,J=11.7), 0.87 (q,1H,J=12.0); $^{13}$C NMR (d$_6$-DMSO) d 142.5, 139.4, 129.7, 126.3, 48.3, 39.4, 21.0; MS (CI/NH$_3$) 609 (M$^+$+18).

B. Preparation of N,N',N"-Trimethyl-1,3,5-cis,cis,-triaminocyclohexane-N,N',N"-tri-p-toluenesulfonyl Amide (6)

Tosylate 5 (5.73 g, 9.7 mmol was dissolved in dry DMF (150 mL), cooled with an ice bath, and NaH (45.2 mmol) was added. After H$_2$ evolution had ceased, dimethylsulfate (12.6 g, 96.9 mmol) was added. The reaction mixture was then heated to ca. 90° C. for 18 h. After cooling, concentrated NH$_4$OH/H$_2$O (1:1) (150 mL) was added and the reaction was stirred for 1 h. The solvents were removed by high vacuum rotary evaporation. The residue was taken up in EtOAc (500 mL), washed with salt solution (100 mL), dried over $Na_2SO_4$, filtered and concentrated to the crude solid product. The pure product was isolated by column chromatography on silica, eluting with $CHCl_3$ (100%). After solvent removal, the product was isolated as a white solid (5.9 g, 96%). Anal. Calcd for $C_{30}H_{39}N_3O_6S_3$; C, 56.82; H, 6.61; N, 6.63. Found: C, 56.58; H, 6.57; N, 6.64. $^1$H NMR ($CDCl_3$) d 7.65 (d,2H,J=8.4) 7.32 (d,2H,J=8.1), 3.90 (m,1H), 2.62 (s,3H), 2.45 (s,3H), 1.40 (m,1H), 1.30 (q,1H, J=11.7); $^{13}$C NMR ($CDCl_3$) d 143.09, 136.65, 129.98, 126.88, 51.96, 31.86, 28.52, 20.99; MS ($CI/NH_3$) 634 ($M^+$+1).

C. Preparation of N,N',N"-Triethyl-1,3,5-cis,cis,-triaminocyclohexane-N,N',N"-tri-p-toluenesulfonyl Amide (7)

Preparation was analogous to 6 from 5 (5.0 g, 8.46 mmol), NaH (39.4 mmol), and diethylsulfate (13.0 g, 84.4 mmol). After analogous workup to give the crude solid product, isolation was accomplished by column chromatography on silica gel, eluting with $MeOH/CHCl_3$ (3/97%). After solvent removal, the product was isolated as a white solid (5.29 g, 93%). Anal. Calcd. for $C_{33}H_{45}N_3O_6S_3$; C, 58.62; H, 6.72; N, 6.22. Found: C, 58.33; H, 6.75; N, 5.96. $^1$H NMR ($d_6$-DMSO) d 7.66 (d,2H,J=7.8), 7.33 (d,2H,J=7.8), 3.82 (br,t, 1H), 3.11 (q,2H,J=6.9), 2.39 (s,3H), 1.58 (q,1H,J=12.9), 1.15 (br.d,1H), 0.99 (t,3H,J=6.6); $^{13}$C NMR ($d_6$-DMSO) d 143.46, 138.26, 129.82, 126.79, 54.60, 39.48, 35.71, 21.33, 16.71; MS ($CI/NH_3$) 693 ($M^+$+18).

D. Preparation of N,N',N"-Trimethyl-1,3,5-cis,cis,-triaminocyclohexanetrihydrobromide (8)

A flask was charged with acetic anhydride (7.5 mL) and cooled in an ice bath. Concentrated HBr (18.5 mL) was added slowly and the solution was allowed to stir at room temperature for 18 h. Tosylate 6 (2.0 g, 3.16 mmol) was added and the suspension was refluxed for 24 h during which a dark red-brown solution formed. The solution was rotary evaporated to leave a dark solid which was taken up in $H_2O$ (25 mL) and extracted with $Et_2O$ (2×50 mL). The aqueous layer was filtered and concentrated to ca. 10 mL. This residue was taken up in 100% EtOH (ca. 50 mL) and an equal amount of $Et_2O$ was added to precipitate the product. The white suspension was cooled at 4° C. for 18 h and then the solid was collected, washed with $Et_2O$, and dried under vacuum (1.15 g, 88%). Anal. Calcd for $C_9H_{21}N_3(HBr)_3$; C, 26.09; H, 5.85; N, 10.14. Found: C, 26.06; H, 5.81; N, 10.06. $^1$H NMR ($D_2O$) d 3.41 (tt,1H,J=12.0,3.6), 2.79 (s,3H), 2.63 (br.d,1H,J=11.4), 1.66 (q,1H,J=12.3); $^{13}$C NMR ($D_2O$) d 55.75, 33.26, 32.51; MS ($CI/NH_3$) 172 ($M^+$+1).

E. Preparation of N,N',N"-Triethyl-cis,cis-1,3,5-triaminocyclohexanetrihydrobromide (9)

Preparation was analogous to 8 from acetic anhydride (16.8 mL), concentrated HBr (30.5 mL), and 7 (5.0 g, 7.4 mmol), with a similar workup using $H_2O$ (50 mL) and $Et_2O$ extraction (3×100 mL). The aqueous layer was filtered and concentrated to near dryness. After precipitation of product from EtOH solution by addition of $Et_2O$ as for 8, the white suspension was cooled at 4° C. for 18 h and then the solid was collected, washed with $Et_2O$, and dried under vacuum (2.73 g, 81%). Anal. Calcd for $C_{12}H_{27}N_3(HBr)_3$; C, 31.57; H, 6.64; N, 9.21. Found: C, 31.49; H, 6.65; N, 9.12. $^1$H NMR ($D_2O$) d 3.47 (tt,1H,J=11.7,3.9), 3.20 (q,2H,J=6.9), 2.62 (br.d,1H,J=10.8), 1.65 (q,1H,J=12.6), 1.31 (t,3H,J=6.9);$^{13}$C NMR ($D_2O$) d 54.40, 43.59, 33.03, 13.60; MS ($CI/NH_3$) 172 ($M^+$+1).

F. Preparation of N,N',N"-Trimethyl-N,N',N"-tris(2-pyridylmethyl)-cis,cis-1,3,5-triaminocyclohexane (($N$-$Me$)$_3$tachpyr)

Triamine 8 (2.0 g, 4.83 mmol) and $Na_2CO_3$ (4.60 g, 43.4 mmol) was suspended in DMF (50 mL) and heated to ca. 80° C. 2-Chloromethylpyridine HCl (2.38 g, 14.51 mmol) in DMF (10 mL) was added in one portion and the reaction was heated for 18 h. The solvent was removed by vacuum rotary evaporation. The residue was taken up in $CHCl_3$ (20 mL) and washed with $H_2O$ (3×100 mL) and once with saturated salt solution (100 mL). After drying over $Na_2SO_4$ and filtration of the drying agent, the solvent was removed to leave the crude product as a dark tarry oil. The product was isolated by column chromatography on silica gel eluting with $MeOH/CHCl_3$ (5/95%) as a brown oil.(0.78 g, 36%). Anal. Calcd. for $C_{27}H_{39}N_6$; C, 72.43; H, 8.80; N, 18.78. Found: C, 72.22; H, 8.62; N, 18.47. $^1$H NMR ($CDCl_3$) d 8.48 (d,1H,J=4.8), 7.59 (dt,1H,J=7.8,1.8), 1.38 (d,1H,J=7.8), 7.08 (t,1H,J=5.7), 3.70 (s,3H), 2.52 (t,1H,J=12.0), 2.22 (s,2H), 2.06 (d,1H,J=10.8), 1.32 (q,1H,J=11.7); $^{13}$C NMR ($CDCl_3$) d 160.48, 149.13, 136.50, 122.72, 121.81, 60.43, 59.82, 37.96, 30.25; MS (FAB/glycerol) 448 ($M^+$+1).

G. Preparation of N,N',N"-Triethyl-N,N',N"-tris(2-methylpyridyl)-cis,cis-1,3,5-triaminocyclohexane (($N$—$Et$)$_3$Tachpyr)

Preparation was analogous to ($N$-$Me$)$_3$tachpyr from 9 (2.73 g,. 5.97 mmol), $Na_2CO_3$ (5.9 g, 55.7 mmol) and 2-chloromethylpyridine HCl (2.95 g, 18 mmol) with analogous workup utilizing $CHCl_3$ (150 mL), $H_2O$ (3×200 mL) and salt solution (100 mL). The pure product was isolated from the dark oil by column chromatography on silica eluting with $MeOH/CHCl_3$ (10/9.0%). Removal of solvent left a light tan oil (0.93 g, 32%). Anal. Calcd for $C_{30}H_{42}N_6$; C, 74.02; H, 8.71; N, 17.27. Found: C, 74.21; H, 8.92; N, 16.97. $^1$H NMR ($CDCl_3$) d 8.49 (d,1H,J=3.9), 7.63 (dt,1H, J=7.8,2.1), 7.53 (d,1H,J=7.8), 7.12 (br.t,1H,J=6.9), 3.77 (s,2H), 2.60 (q,3H,J=7.8, one proton by integral is obscured), 1.97 (br.d,1H,J=8.7), 1.28 (q,1H,J=12.0), 0.98 (t,3H,J=6.9);$^{13}$C NMR ($CDCl_3$) d 162.12, 148.76, 136.38, 122.41, 121.56, 57.63, 56.18, 45.06, 30.98, 14.04; MS ($CI/NH_3$) 487 ($M^+$+1).

EXAMPLE 6

Electrochemical Studies-Detection of Hydroxyl Radical from Fe-tachpyr and $H_2O_2$ A solution of 0.5 mM 2a/3a in $H_2O$ with KCl (0.5 M) as supporting electrolyte was studied by cyclic voltammetry. By measurement of supporting electrolyte alone, a working potential range of 0.11 V to 1.29 V/NHE was established, that is bounded by reduction of $O_2$ and oxidation of $Cl^-$ (FIG. 6). Complexes 2a/3a exhibited an oxidative wave at 0.54 V/SCE that was studied by variation of electrode rotation speed and monitoring of ring current. Thus, Fe-tachpyr complex are redox-active.

In order to investigate whether the imino complexes mixture 2/3 catalyzes HO. formation from $H_2O_2$ the deoxyribose assay was conducted. To a buffered (HBSS) solution of 2a/3a (100 mM), deoxyribose (5 mM) and $H_2O_2$ (200 mM) were mixed to give one mL of solution with final concentrations as stated. The mixture was incubated at 37° C. for 30 min followed by quenching with 1.0 mL of trichloroacetic acid (6% w/v) and 0.5 mL of thiobarbituric acid (1% w/v in 0.5 M NaOH). The mixture was boiled for 15 min at 97° C. The UV spectrum at 532 nm of the solution revealed an absorbance (0.108) indicative of oxidative degradation of deoxyribose. Using $Fe(NH_4)_2(SO_4)_2$ in place of 2a/3a afforded an absorbance of 0.205. Therefore, the toxicity of tachpyr may be related to intracellular formation of imino complexes that potentiate oxidative cell damage.

EXAMPLE 7

Reaction of Fe(III)-ATP (1:3) Complex with Tachpyr

To a solution of ATP disodium salt (1.82 g, $3.30 \times 10^{-3}$ mol) in 0.1 M HEPES/Na buffer (pH 7.0, 20 mL) was added 6.14 mL of $FeCl_3$ (0.179 M) solution in 1 M HCl (pale yellow), while maintaining the pH at 7.0 using 1.0 N NaOH. A deeper yellow solution was obtained. The total volume was made up to 100 mL. To this Fe-ATP complex solution (1 mL) was added tachpyr (3 eq based on Fe, 0.0133 g, $3.3 \times 10^{-5}$ mol) in 10 mL distilled water giving a color change from yellow to green after 5 min. After 48 h the reaction was complete as judged by UV-Vis spectroscopy, which identified the products as 2a and 3a.

EXAMPLE 8

Cytotoxicity Assays Using Tachpyr

A. MTT Assays

The cytotoxic effects of tachpyr on mouse (MBT2) and human (T24) bladder cancer cells were evaluated in vitro, and compared to normal human fibroblasts (MRC-5). MBT2 cells were provided by Dr. L. Lattime (Thomas Jefferson University, Philadelphia, Pa.), while MRC-5 cells were a gift of H. Blau (Standford University, Standford, Calif.). T24 cells were obtained from ATTC (Rockville, Md.). Cells were grown in RPMI (MBT2) or DME medium (T24 and MRC-5) containing 10% fetal bovine serum in a humidified chamber containing 5% $CO_2$. $5 \times 10^3$ cells were plated into 96-well tissue culture dishes, and permitted to attach overnight. Test compounds were then added, with six replicate cultures used for each point.

After 72 hours, cell viability was assessed using an MTT dye reduction assay [Mosmann, T., J. Immunol. Meth. 65:55 (1983)]. The MTT assay is widely used to measure drug effects on cell viability. [see Richardson, D., Blood 86:4295 (1995); Brüggerman, S., Cancer Res. 57:2676 (1997); and Silber, R., Blood 84:3440 (1994)]. Specifically, (3-(4,5-dimethylthiazol-2-yl)-2,5-diphenyl tetraxolium bromide was added to the medium, and the formation of a reduced product was assayed by measuring the optical density at 560/650 nm after 3 hours. Color formation was considered proportional to viable cell numbers. $IC_{50}$ was defined as the concentration required to inhibit viability by 50%, and was calculated using the Multiple Drug-effect Analysis Program (Biosoft).

Results demonstrated that both tachpyr and desferrioxamine were cytotoxic to MBT2 cells, and tachpyr was more cytotoxic than desferrioxamine. In four independent experiments, the average IC50 of tachpyr was $4.6 \pm 2.0$ $\mu$M (standard error), as compared to 70 $\mu$M for desferrioxamine.

Figure 8:
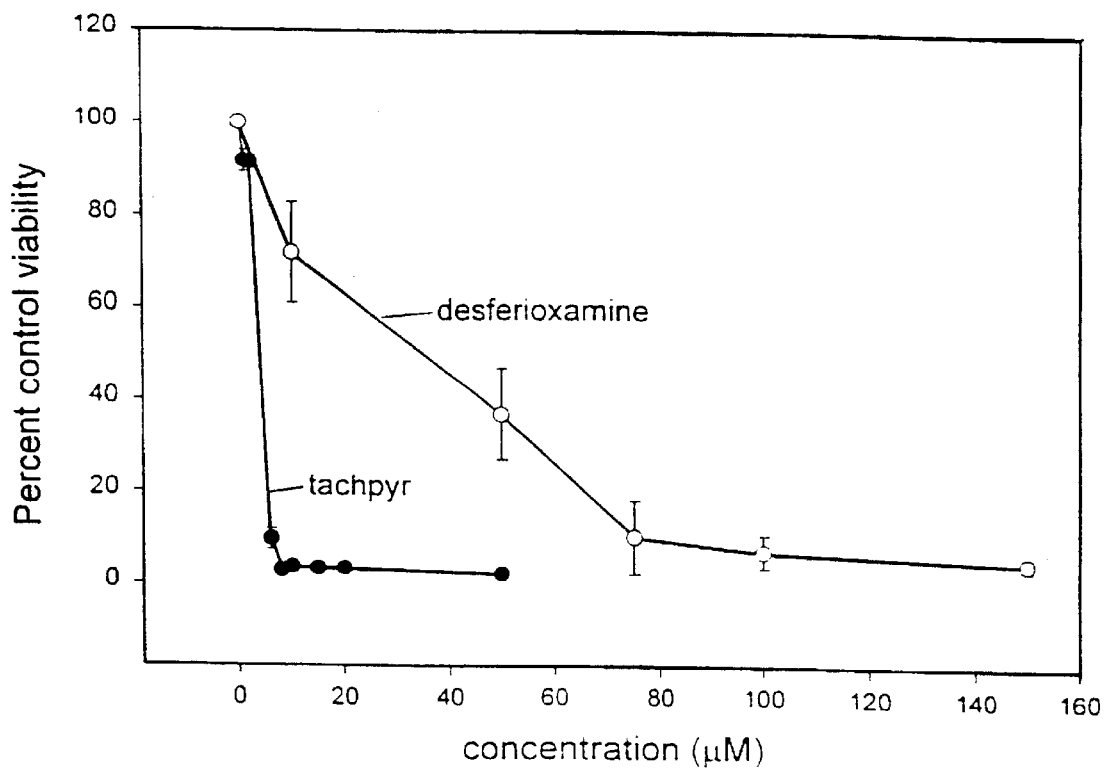
FIG. 8 illustrates the comparative cytotoxicity of varying doses of tachpyr and desferioxamine on cultured MBT2 bladder cancer cells. Cells were incubated with varying doses of desferioxamine mesylate for 72 hours, and viability was assessed using an MTT assay that is described in Example 8.

FIG. 8 illustrates the comparative cytotoxicity of tachpyr and desferrioxamine on cultured MBT2 cells. From the figure, it is clear that cell growth was inhibited by both by tachpyr (with a calculated $IC_{50}$ of 3.6 $\mu$M from this data) and desferrioxamine (70 $\mu$M), and that tachpyr was more potent than desferrioxamine. The cytotoxic effects of tachpyr were not cell specific, as T24 bladder cancer cells were also sensitive to tachpyr as shown in Table I below. Tachpyr was also cytotoxic to breast cancer cell lines. MRC-5 normal human human fibroblasts were sensitive to tachpyr, however, the $IC_{50}$ was substantially higher (30.5 $\mu$M). This suggests that tumor cells maybe more sensitive to tachpyr than non-tumor cells, and is consistent with the application in anti-tumor therapy. Rather, both T24 bladder cancer cells and MRC-5 normal human fibroblasts were sensitive to tachpyr, with $IC_{50}$ values of 4.3 $\mu$M and 30.5 $\mu$tM, respectively.

TABLE I

| Cell Type | $IC_{50}(\mu M)$ of Tachpyr |
| --- | --- |
| MBT2 | 2.2 |
| T24 | 4.3 |
| MRC-5 | 30.5 |

In general, tachpyr was profoundly cytotoxic to cultured bladder tumor cells at concentrations over 8 $\mu$M.

B. Clonogenic Assays

Cell viability was also-assessed using a clonogenic assay, which measures the ability of cells to divide and form visible colonies of about 50 or more cells. Replicate plates were exposed to various concentrations of tachpyr added to the growth medium. Control cells received no tachpyr. At the end of the incubation period, the surviving cells were trypsinized, diluted, and re-plated in growth medium without tachpyr. Colonies were permitted to grow for seven days. The growth medium was then removed, and plates were fixed with 0.5% gluteraldehyde, stained with 1% crystal violet, and then counted.

Figure 9:
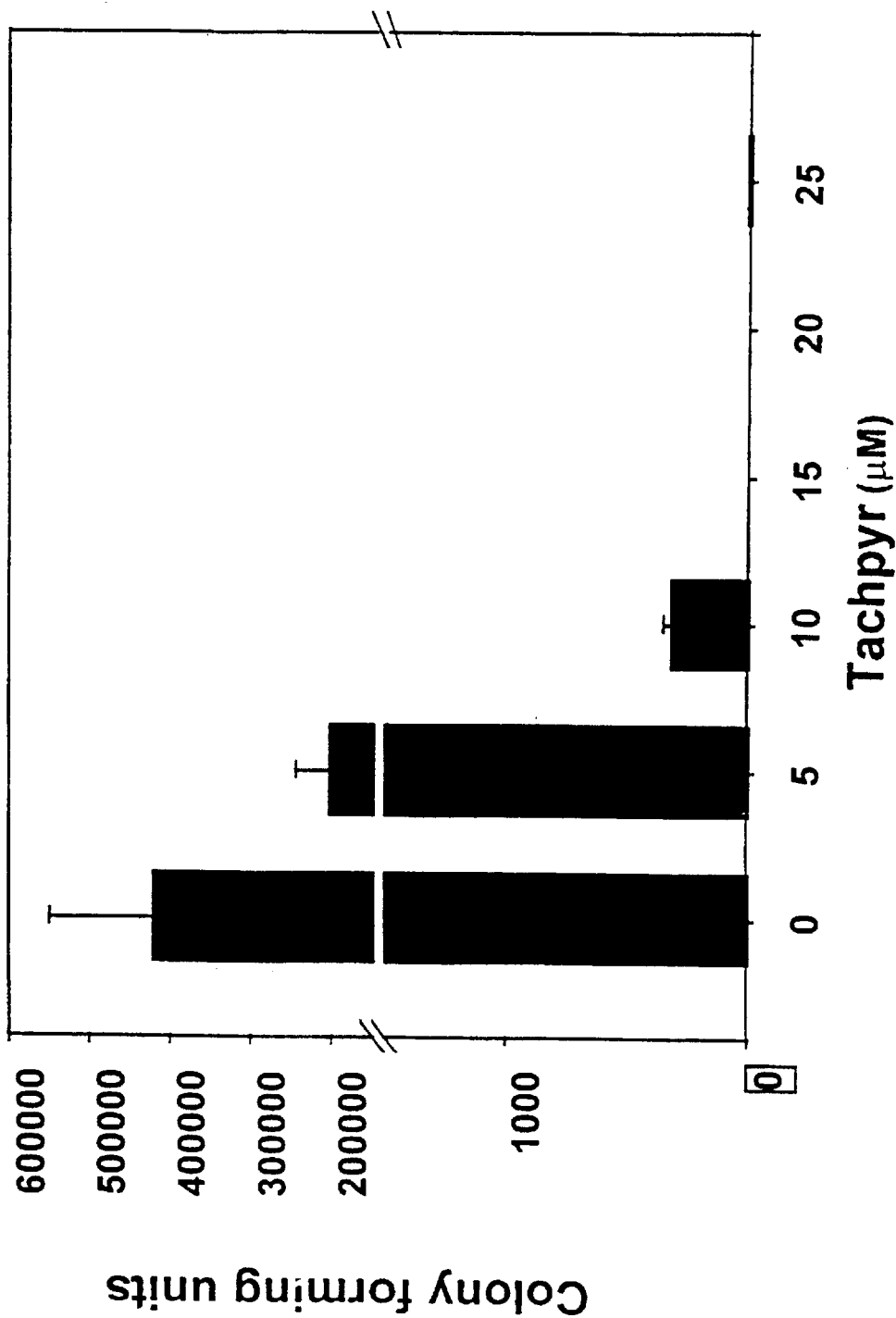
FIG. 9 illustrates the effect of tachpyr on colony formation in MBT2 cells. Cells were incubated for 72 hours with tachpyr, and viability was assessed using a clonogenic assay.

As shown in FIG. 9, tachpyr inhibited colony formation in MBT2 cells. These results confirmed that viability was sharply reduced by tachpyr as was also indicated by the MTT assays.

C. Time Course of Cytotoxicity

Figure 10:
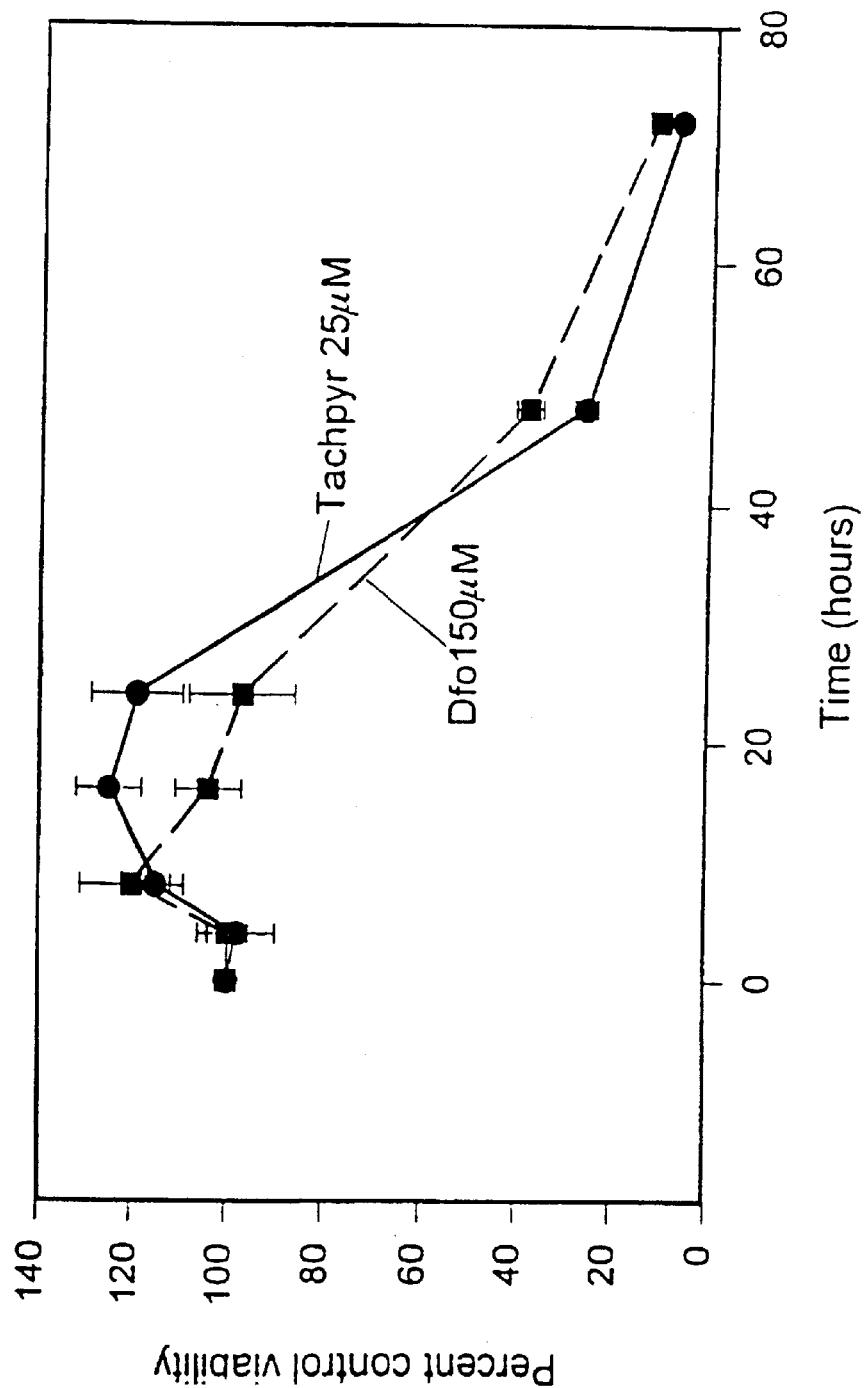
FIG. 10 illustrates the time course of cytotoxicity for tachpyr. Cells were incubated with 150 $\mu$M desferioxamine (dfo) or 25 $\mu$M tachpyr for various lengths of time and survival measured using an MTT assay.

MBT2 cells were then incubated with 150 $\mu$M (dfo) or 25 $\mu$M tachpyr for various lengths of time, and survival was then measured using the MTT assay described above. Viability at time 0 was defined as 100%. As shown in FIG. 10, tachpyr was not immediately cytotoxic to cells. Rather, cytotoxicity was delayed by approximately 24 hours, paralleling the cytotoxic time course of desferrioxamine.

EXAMPLE 9

Ferritin Synthesis

Ferritin is a major iron storage protein whose synthesis is dependent upon intracellular concentrations of iron. To examine the role of tachpyr in the chelation of intracellular iron, the influence of tachpyr on ferritin synthesis was examined. Cells were exposed for either 7 or 16 hours to media containing either no additions, 20 $\mu$M tachpyr, 150 $\mu$M desferrioxamine or 200 $\mu$M ferric nitrolotriacetate. During the last two hours of incubation, cells were metabolically labeled with [35] S-translabel (ICN) and ferritin visualized by immunoprecipitation and SDS PAGE [Torti, S. et al.,J. Biol. Chem. 263:12638 (1988).]

Figure 11:
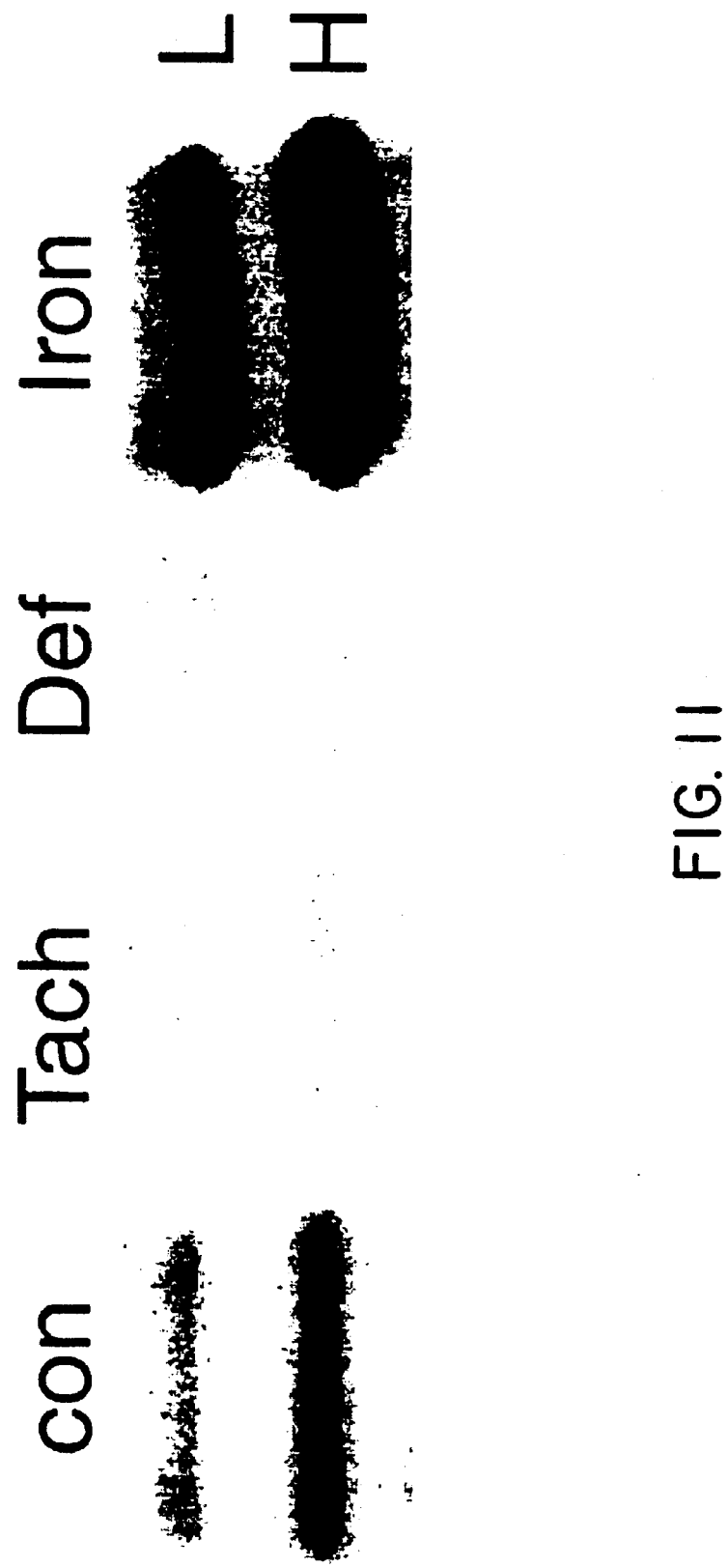
FIG. 11 illustrates the effect of tachpyr on ferritin synthesis. Cells were treated with 20 $\mu$M tachpyr (tach), or 150 $\mu$M desferioxamine (def), or 200 $\mu$M ferric nitrilotriacetate (iron) in growth medium for 16 hours. Cells were labeled with [$^{35}$]S amino acids for the last 2 hours of treatment. Ferritin was isolated by immunoprecipitation and analyzed by SDS PAGE. The H and L subunits of ferritin are shown (lower and upper bands, respectively).

As shown in FIG. 11, ferritin synthesis was repressed in cells treated for 16 hours with tachpyr. Under these conditions, tachpyr repressed ferritin synthesis as effectively as desferrioxamine. The H and L subunits of ferritin are shown (lower and upper bands, respectively). As established by consistent TCA-precipitable counts, the ferritin synthesis was specifically inhibited by tachpyr. A similar inhibition of ferritan synthesis was also seen after 7 hours, a time point preceding all cytotoxic effects of tachpyr. Thus, intracellular iron depletion is likely an early, proximal event initiated by tachpyr.

EXAMPLE 10

Partition Coefficient

Lipophilicity was measured by the value of the partition coefficient obtained on partition between n-octanol and water. Lipophilicity calculations yielded a partion coefficient (log $P_{oct/H2O}$) of −0.10, indicating that tachpyr has the potential to penetrate :k the cell membrane and chelate intracellular ion. This observation is consistent with the tachpyr's inhibition of ferritin synthesis previously shown in Example 9.

Without being bound to any particular theory, results suggest that the profound toxicity of tachpyr relative to desferioxamine may be attributable, in part, to the enhanced permeability of tachpyr relative to desferioxamine. Alternatively or perhaps additionally, tachpyr may have greater access to key intracellular ion pools.

EXAMPLE 11

Effect of Metal Complexes of Tachpyr on Cell Viability

The metal complexes of tachpyr were prepared as disclosed in Example 3, and their effects on MBT2 cells were compared to those of tachpyr after 72 hours using the MTT assay referenced in Example 8.

Figure 12:
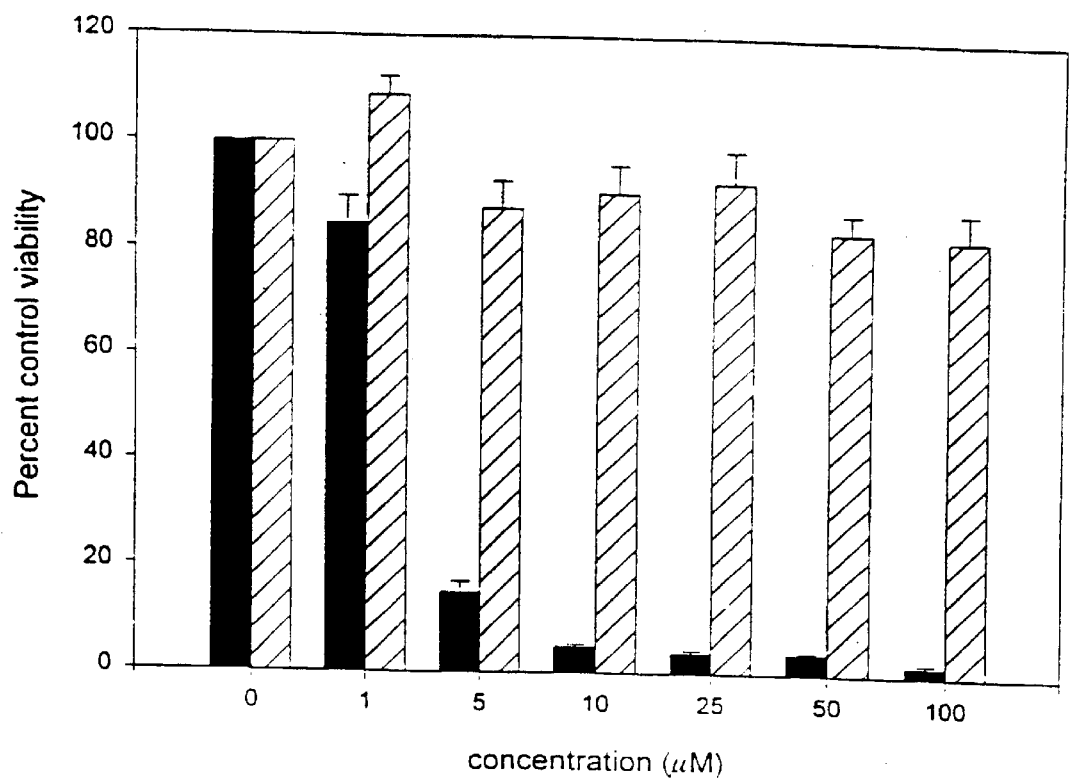
FIG. 12 illustrates the effect of tachpyr and Fe[tachpyr]Cl$_2$ on MBT2 cells. Cells were treated for 72 hours with either tachpyr (solid bars) or Fe[tachpyr]Cl$_2$ (striped bars) before viability was assessed using an MTT assay.
Figure 13:
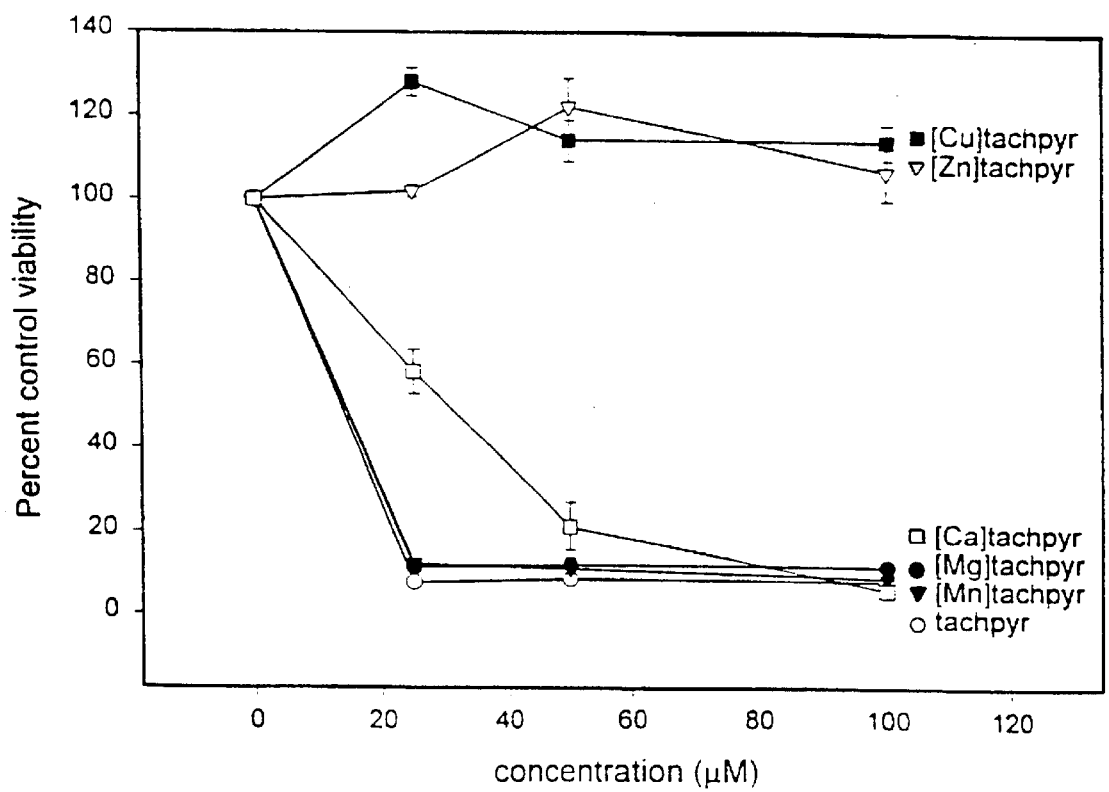
FIG. 13 shows the effect of tachpyr and its metal derivatives on MBT2 cells. Viability was assessed after 72 hours of exposure to the compounds indicated.

FIG. 12 illustrates the comparative cytotoxicity of tachpyr (solid bars) and Fe[tachpyr]Cl$_2$ (striped bars). FIG. 13 illustrates the comparative cytoxicity of tachpyr, [Mg] tachpyr, [Mn]tachpyr, [Cu]tachpyr, [Zn]tachpyr, and [Ca] tachpyr.

In general, the Ca(II), MN(II) and MG(II) complexes of tachpyr were toxic, whereas the Zn(II), FE(II) and CU(II) complexes were not toxic.

EXAMPLE 12

Effect of Sterically Hindered Derivatives of Tachpyr on Cell Viability

Alkylated derivatives of tachpyr were prepared as indicated in Example 2, with methyl or ethyl groups substituted for hydrogen at the amino nitrogens N1, N2 and N3. These derivatives were unable to strongly bind FE(III) or Fe(II), but were able to bind ZN(II) and Cu(II).

Figure 14:
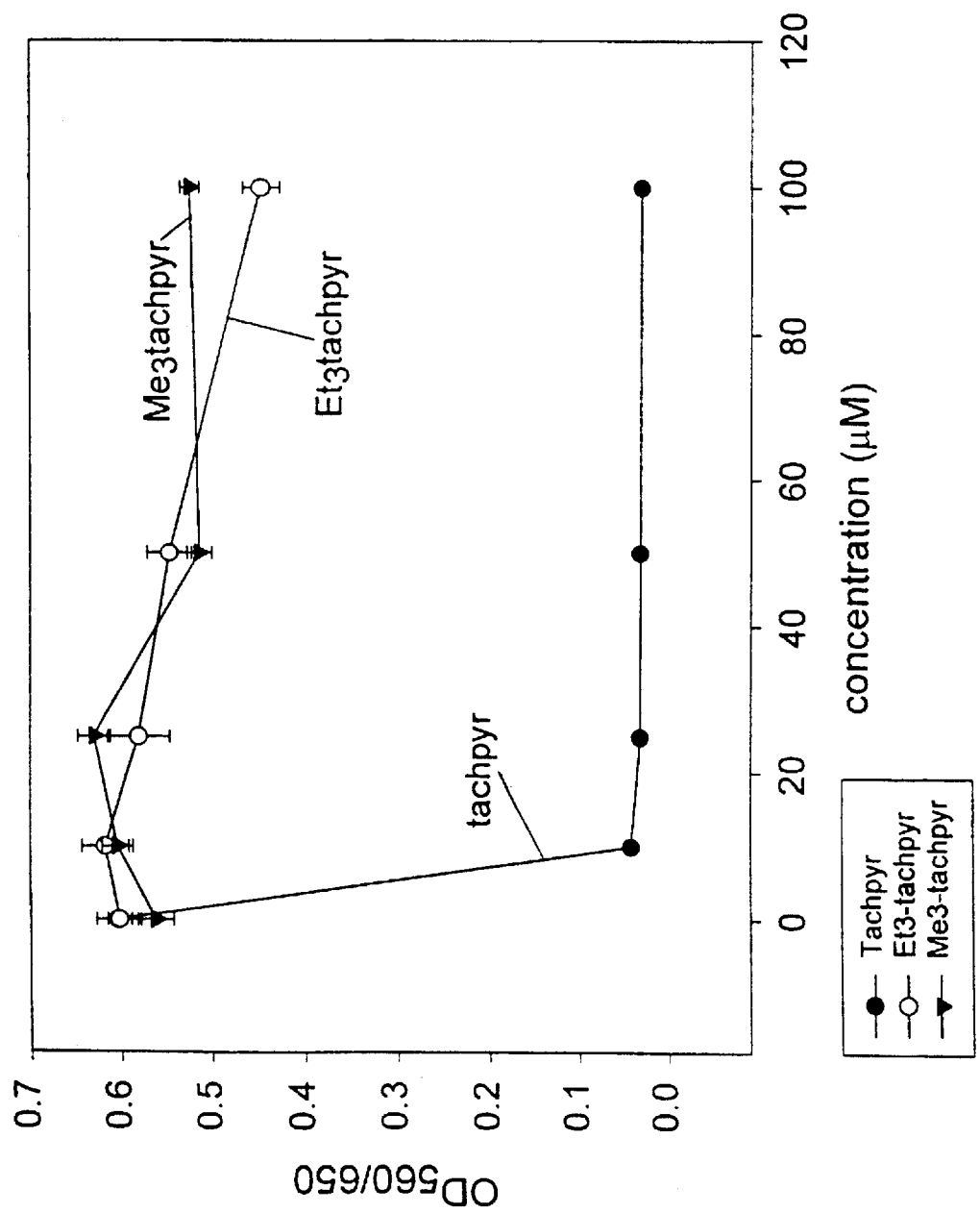
FIG. 14 shows the effect of N-alkylated derivatives of tachpyr on cultured MBT2 cells. Viability was assessed after 72 hours of exposure to the compounds indicated.
Figure 15A:
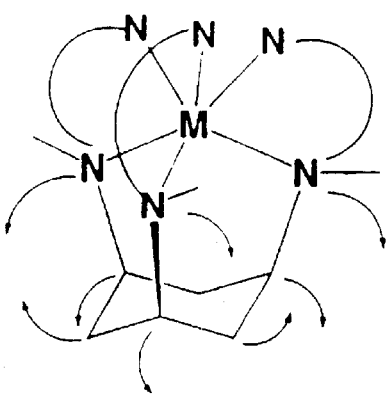
FIG. 15A depicts the flattening distortion of the tachpyr cyclohexyl ring and corresponding torsion angles as a measure of distortion of coordinated tach ligand.
Figure 15A:
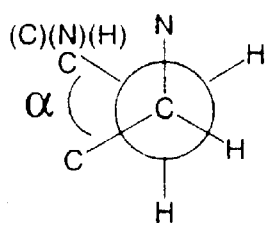
Figure 15B:
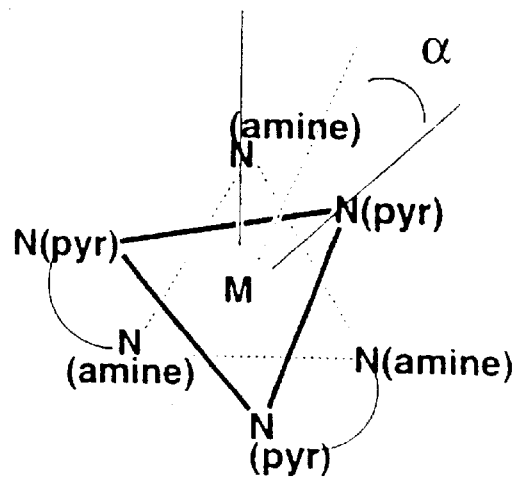
FIG. 15B depicts twist angles as a measure of distortion of coordinated tach ligand, wherein the twist angle a is defined for the coordination sphere of M(tachpyr)$^{n+}$.

FIG. 14 compares the cytotoxicity of these alkylated derivatives with that of tachpyr on MBT2 cells. From the results, it is clear that these sterically hindered tachpyr derivatives were non-toxic, suggesting that tachpyr is an iron chelator.

EXAMPLE 13

Relationship of Bond Length to Metal Radius

To examine the chemical and structural effects of alkylation on complexation properties, the single-crystal x-ray structures of the Ni(II) complexes Ni[tachpyr]Cl$_2$ and Ni[(N-Me)$_3$tachpyr][ClO$_4$]$^2$ were compared. The bond distance between the metal and the amine nitrogens of the respective tachpyr chelator was lengthened from 2.102(4) to 2.168 Å upon methylation of tachpyr. The lengthening demonstrates the steric effect of the methyl group on nitrogen, which weakens the association of alkylated tachpyr with the metal ions, steric and electronic effects on H$^a$ are important in the process steric and electronic effects on H$^a$ are important in the process and particularly with the iron.

As shown below, Table 2 shows the relationship between bond length and metal radius for metal derivatives of tachpyr.

Table 3 shows the relationship between the metal radius and the twist and torsion angles of coordinated tachpyr.

TABLE 2

Metal-tachpyr Bond Lengths Correspond to Metal Radius

| complex | $^rM^{n+}$,Å | $^dM$–N9pyr,Å | $^dM$–N (tach),Å |
|---|---|---|---|
| Ni(tachpry)Cl$_2$Me OH | 0.83 | 2.118(4) | 2.099(4) |
| | | 2.122(4) | 2.099(4) |
| | | 2.127(4) | 2.107(4) |
| Zn(tachpyr) | 0.88 | 2.165(4) | 2.160(3) |
| | | 2.165(4) | 2.160(3) |
| | | 2.165(4) | 2.160(3) |
| Ga(tachpyr) (NO$_3$)$_3$ DMF | 0.76 | 2.090(5) | 2.056(5) |
| | | 2.105(5) | 2.079(5) |
| | | 2.114(5) | 2.083(4) |
| In(tachpyr) (NO$_3$)$_3$ DMSO | 0.94 | 2.238(2) | 2.222(2) |
| | | 2.234(2) | 2.248(2) |
| | | 2.257(2) | 2.253(2) |

*C.N. = 6, R. D. Shannon, Acta Cryst., 1976, A32, 751.

TABLE 3

Metal Radius Influences Twist and Torsion Angles of Coordinatedtachpyr

| complex | $^rM^{n+}$,Å | twist angle, deg | cyclohexyl C-C-C-C torsion angle, min/max/ave, deg |
|---|---|---|---|
| Ni(tachpry)Cl$_2$Me OH | 0.83 | 44.65(76) | 49.55(56) |
| | | 45.59(72) | 53.98(54) |
| | | 46.31(76) | 51.96 |
| Zn(tachpyr) (ClO$_4$)$_2$ Me OH | 0.88 | 42.75(64) | 52.32(63) |
| | | 43.75(64) | 52.38(64) |
| | | 43.76(64) | 52.35 |
| Ga(tachpyr) (NO$_3$)$_3$ DMF | 0.76 | 43.96(88) | 49.7(7) |
| | | 45.16(84) | 55.2(6) |
| | | 45.32(88) | 52.3 |
| In(tachpyr) (NO$_3$)$_3$ DMSO | 0.94 | 35.86(44) | 46.8(3) |
| | | 36.00(40) | 52.4(3) |
| | | 38.04(40) | 49.6 |

EXAMPLE 14

Apoptosis

Figure 16:
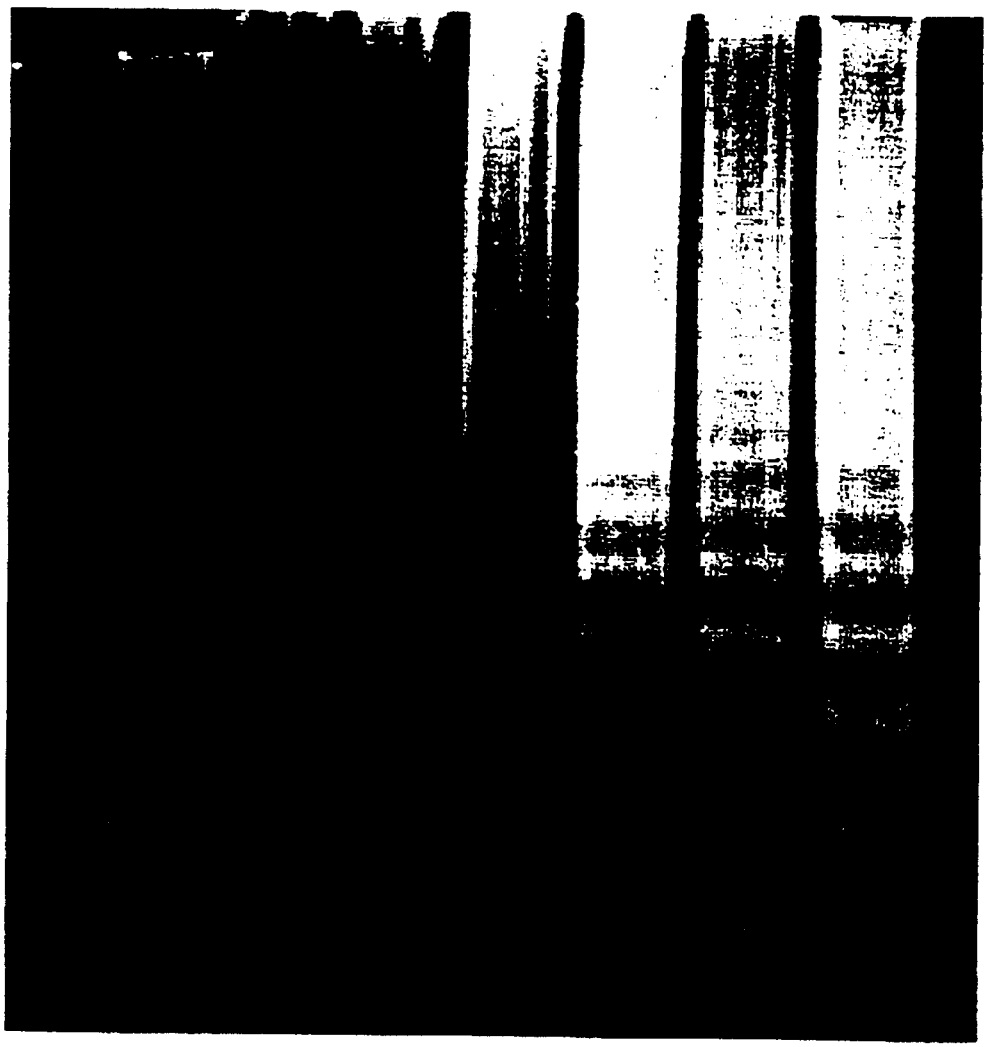
FIG. 16 illustrates the apoptotic effects on DNA of cells treated with tachpyr, etoposide (vp) and cisplatin (cis) at 0, 6, 12 and 20 hours.

Apoptosis, or "programmed cell death," is a process initiated by many anti-cancer agents. Pathways of apoptosis involve complex intracellular changes, including the action of intracellular proteases (caspases), release of cytochrome C, mitochondrial changes, nuclear condensation and fragmentation, and ultimately cell death. A hallmark of apoptotic cell death is the appearance of "DNA ladders": DNA cleaved at intranucleosomal regions to generate a series of DNA fragments that can be visualized using agarose gel electrophoresis. In order to determine whether tachpyr triggers apoptotic pathways, DNA was isolated from RAW 264.7 cells that had been treated with 25 $\mu$M tachpyr for 0, 6, 12 and 20 hours. DNA was also isolated from cells treated for 7 hours with 50 $\mu$M cisplatin or 500 $\mu$M etoposide (VP16). Cisplatin and etoposide are DNA damaging agents that are currently used in cancer therapy and are known to induce apoptosis. They served as positive controls. We compared the effects of tachpyr, VP16 and cisplatin on DNA fragmentation using agarose gel electrophoresis. As shown in FIG. 16, tachpyr clearly induced DNA fragmentation consistent with apoptotic cell death. The magnitude of the effect was roughly comparable to that of VP16 and cisplatin. Thus, cytotoxic pathways elicited by tachpyr are similar to those evoked by classic anti-cancer agents, and are consistent with its contemplated use as a chemotherapeutic agent.

All references referred to herein are hereby incorporated by reference in their entirety.

It should be understood that various changes and modifications to the presently preferred embodiments described herein, will be apparent to those skilled in the art.

Such changes and modifications can be made without departing from the spirit and scope of the present invention and without diminishing its attendant advantages. It is therefore intended that such changes and modifications be covered by the appended claims.

What is claimed is:

1. A family of hexadentate Fe(II) chelators, said Fe(II) chelators being represented by the formulas below:

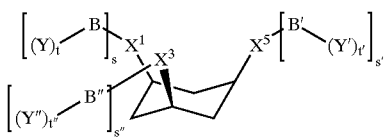

wherein:

$X^1$, $X^3$, and $X^5$ are N, O or S, wherein the $X^1$, $X^3$, and $X^5$ atoms are at the 1, 3, and 5 positions of a cyclohexyl group and are in a cis, cis disposition;

B, B', and B" are aryl groups;

Y, Y', and Y" contain N, O, or S atoms that originate from either aliphatic, branched aliphatic, aryl, or heterocyclic groups, or any combination thereof, and/or Y, Y' and Y" are $NH_2$ or NHR, OH, or SH, $CO_2H$, $P(O)(OH)_2$, RP(O)OH, ROP(O)OH groups or any combination thereof, and R is H, aliphatic, branched aliphatic, or aryl groups, or any combination thereof that may or may not be identical in Y, Y' and Y";

s, s', and s" are 1 to about 2; and t, t', and t" are 1 to about 2;

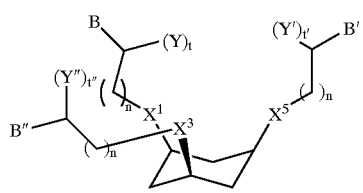

wherein:

$X^1$, $X^3$, and $X^5$ are N, O or S, wherein the $X^1$, $X^3$, and $X^5$ atoms are at the 1, 3, and 5 positions of a cyclohexyl group and are in a cis, cis disposition;

B, B', and B" are aryl groups;

Y, Y' and Y" contain N, O, or S atoms that originate from either aliphatic, branched aliphatic, aryl, or heterocyclic groups, or any combination thereof, or $NH_2$ or NHR, OH, or SH, $CO_2H$, $P(O)(OH)_2$, RP(O)OH, ROP(O)OH groups or any combination thereof, and R is H, aliphatic, branched aliphatic, or aryl groups, or any combination thereof that may or may not be identical in Y, Y' and Y";

t, t', and t" are 1 to about 2; and n is between 0 and about 3;

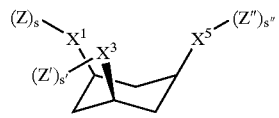

wherein:

$X^1$, $X^3$, and $X^5$ are N, O or S, wherein the $X^1$, $X^3$, and $X^5$ atoms are at the 1, 3, and 5 positions of a cyclohexyl group and are in a cis, cis disposition; and s, s', s" are 1 to about 2;

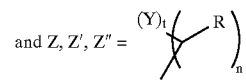

wherein:

R is H, aliphatic, branched aliphatic, or aryl groups, or any combination thereof that may or may not be identical in Z, Z' and Z";

Y is $NH_2$ or NHR', OH, or SH, $CO_2H$, $P(O)(OH)_2$, R'P(O)OH, R'OP(O)OH groups, or any combination thereof, and R' is H, aliphatic, branched aliphatic, or aryl groups, or any combination thereof, or Y is a group containing N, O, or S atoms that originate from either aliphatic, branched aliphatic, aryl, heterocyclic groups, or any combination thereof, in any case, Y and R' may or may not be identical in Z, Z' and Z";

t is 1 to about 2; and n is between 0 and about 3.

2. The family of hexadentate Fe(II) chelators in accordance with claim 1, wherein the Fe(II) chelators are selected from the group consisting of tach-C(Me)pyr, tach-6-Mepyr, tachquin, s,s,s-tachem-2Bn, s,s,s-tachen-2Me, (N—R)$_3$tachpry, tachpyr-2H$_2$ and tach-N-Me-Im-imine.

3. The family of hexadentate Fe(II) chelators in accordance with claim 1, wherein each chelator is formulated in a therapeutic dosage singly, in combination with at least one pharmaceutical or chemically linked to at least one pharmaceutical.

4. The family of hexadentate Fe(II) chelators in accordance with claim 1, wherein the chelators are each in combination with pharmaceutically acceptable carriers, diluents, stabilizers, solubilizers, lubricants, binders, or excipients.

5. The family of hexadentate Fe(II) chelators in accordance with claim 1, wherein the chelators exhibit antiproliferative activity against tumor cells.

6. A pharmaceutical composition for treating and preventing medical conditions in mammals, the composition being capable of binding intracellular iron and comprising as active ingredient a compound of the formula:

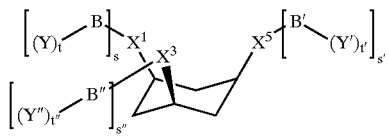

wherein:
X¹, X³, and X⁵ are N, O or S, wherein the $X^1$, $X^3$, and $X^5$ atoms are at the 1, 3, and 5 positions of a cyclohexyl group and are in a cis, cis disposition;

B, B', and B" are aryl groups;

Y, Y' and Y" contain N, O, or S atoms that originate from either aliphatic, branched aliphatic, aryl, or heterocyclic groups, or a combination thereof, and/or Y, Y' and Y" are $NH_2$ or NHR, OH, or SH, $CO_2H$, $P(O)(OH)_2$, RP(O)OH, ROP(O)OH groups or a combination thereof, and R is H, aliphatic, branched aliphatic, or aryl groups, or a combination thereof that may or may not be identical in Y, Y' and Y";

s, s', and s" are 1 to about 2; and t, t', and t" are 1 to about 2.

7. The pharmaceutical composition in accordance with claim 6, wherein the active ingredient compound is selected from the group of metal chelators consisting of tach-C(Me)pyr, tach-6-Mepyr, tachquin, sss-tachem-2Bn, sss-tachen-2Me, (N—R)₃tachpyr, tachpyr-$2H_2$ and tach-N-Me-Imimine.

8. The pharmaceutical composition in accordance with claim 6, wherein the composition is a chemotherapeutic agent.

9. The pharmaceutical composition in accordance with claim 6, wherein the composition is formulated in a therapeutic dosage by itself, in combination with at least one other pharmaceutical, or chemically linked to at least one other pharmaceutical.

10. The pharmaceutical composition in accordance with claim 6, wherein the composition is in combination with pharmaceutically acceptable carriers, diluents, stabilizers, solubilizers, lubricants, binders and the like or excipients thereof.

11. The pharmaceutical composition in accordance with claim 6, wherein the composition comprises a mammalian metabolic conjugate of the active ingredient compound.

12. The pharmaceutical composition in accordance with claim 6, wherein the medical conditions include, but are not limited to, cancer, inflammatory and infectious conditions, vasoreactive and vasoocclusive conditions, coronary and peripheral athlerosclerosis, parasitic diseases, neurologic and neuromuscular conditions, and viral conditions including AIDS.

13. The pharmaceutical composition in accordance with claim 12, wherein the medical conditions further include vasospasm, Parkinson's disease, Alzeihmer's disease, malaria, tuberculosis, arthritis, allergic and asthmatic conditions, hepatitis, coronary and peripheral vascular ischemia-reperfusion injury of blood vessels.

14. The pharmaceutical composition in accordance with claim 6, wherein the composition is orally formulated in combination with a liquid diluent or a solid carrier.

15. The pharmaceutical composition in accordance with claim 6, wherein the therapeutically effective dosage of the composition prevents the occurrence of, reduces the rate of growth of, or diminishes the size of tumor cells or any combination thereof.

16. A pharmaceutical composition for treating and preventing medical conditions in mammals, the composition being capable of binding intracellular iron and comprising as active ingredient a compound of the formula:

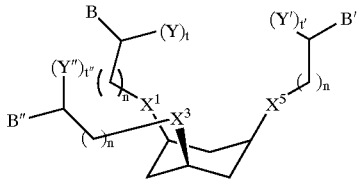

wherein:
X¹, X³, and X⁵ are N, O or S, wherein the $X^1$, $X^3$, and $X^5$ atoms are at the 1, 3, and 5 positions of a cyclohexyl group and are in a cis, cis disposition;

B, B', and B" are aryl groups;

Y, Y' and Y" contain N, O, or S atoms that originate from either aliphatic, branched aliphatic, aryl, or heterocyclic groups, or any combination thereof, or $NH_2$ or NHR, OH, or SH, $CO_2H$, $P(O)(OH)_2$, RP(O)OH, ROP(O)OH groups or any combination thereof, and R is H, aliphatic, branched aliphatic, or aryl groups, or any combination thereof that may or may not be identical in Y, Y' and Y";

t, t', and t" are 1 to about 2; and n is between 0 and about 3.

17. The pharmaceutical composition in accordance with claim 16, wherein the active ingredient compound is selected from the group of metal chelators consisting of sss-tachen-2Bn and sss-tachen-2Me.

18. The pharmaceutical composition in accordance with claim 16, wherein the composition is a chemotherapeutic agent.

19. The pharmaceutical composition in accordance with claim 16, wherein the composition is formulated in a therapeutic dosage by itself, in combination with at least one other pharmaceutical, or chemically linked to at least one other pharmaceutical.

20. The pharmaceutical composition in accordance with claim 16, wherein the composition is in combination with pharmaceutically acceptable carriers, diluents, stabilizers, solubilizers, lubricants, binders and the like or excipients thereof.

21. The pharmaceutical composition in accordance with claim 16, wherein the composition comprises a mammalian metabolic conjugate of the active ingredient compound.

22. The pharmaceutical composition in accordance with claim 16, wherein the medical conditions include, but are not limited to, cancer, inflammatory and infectious conditions, vasoreactive and vasoocclusive conditions, coronary and peripheral athlerosclerosis, parasitic diseases, neurologic and neuromuscular conditions, and viral conditions including AIDS.

23. The pharmaceutical composition in accordance with claim 22, wherein the medical conditions further include vasospasm, Parkinson's disease, Alzeihmer's disease, malaria, tuberculosis, arthritis, allergic and asthmatic conditions, hepatitis, coronary and peripheral vascular ischemia-reperfusion injury of blood vessels.

24. The pharmaceutical composition in accordance with claim 16, wherein the composition is orally formulated in combination with a liquid diluent or a solid carrier.

25. The pharmaceutical composition in accordance with claim 16, wherein the therapeutically effective dosage of the composition prevents the occurrence of, reduces the rate of growth of, or diminishes the size of tumor cells or any combination therof.

26. A pharmaceutical composition for treating and preventing medical conditions in mammals, the composition being capable of binding intracellular iron and comprising as active ingredient a compound of the formula:

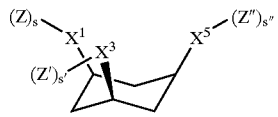

wherein:
 $X^1$, $X^3$, and $X^5$ are N, O or S, wherein the $X^1$, $X^3$, and $X^5$ atoms are at the 1, 3, and 5 positions of a cyclohexyl group and are in a cis, cis disposition; and
 s, s', s'' are 1 to about 2;

and Z, Z', Z'' = 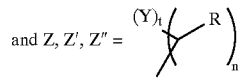

wherein:
 R is H, aliphatic, branched aliphatic, or aryl groups, or any combination thereof that may or may not be identical in Z, Z' and Z'';
 Y is $NH_2$ or NHR', OH, or SH, $CO_2H$, $P(O)(OH)_2$, R'P(O)OH, R'OP(O)OH groups, or any combination thereof, and R' is H, aliphatic, branched aliphatic, or aryl groups, or any combination thereof, or Y is a group containing N, O, or S atoms that originate from either aliphatic, branched aliphatic, aryl, heterocyclic groups, or any combination thereof, in any case, Y and R' may or may not be identical in Z, Z' and Z'';
 t is 1 to about 2; and
 n is between 0 and about 3.

27. The pharmaceutical composition in accordance with claim 26, wherein the active ingredient compound is selected from the group of metal chelators consisting of tach-C(Me)pyr, tach-6-Mepyr, tachquin, (N—R)₃tachpyr, tachpyr-H₂ tachpyr-2H₂ and tach-N-Me-Im-imine.

28. The pharmaceutical composition in accordance with claim 26, wherein the composition is a chemotherapeutic agent.

29. The pharmaceutical composition in accordance with claim 26, wherein the composition is formulated in a therapeutic dosage by itself, in combination with at least one other pharmaceutical, or chemically linked to at least one other pharmaceutical.

30. The pharmaceutical composition in accordance with claim 26, wherein the composition is in combination with pharmaceutically acceptable carriers, diluents, stabilizers, solubilizers, lubricants, binders and the like or excipients thereof.

31. The pharmaceutical composition in accordance with claim 26, wherein the composition comprises a mammalian metabolic conjugate of the active ingredient compound.

32. The pharmaceutical composition in accordance with claim 26, wherein the medical conditions include, but are not limited to, cancer, inflammatory and infectious conditions, vasoreactive and vasoocclusive conditions, coronary and peripheral athlerosclerosis, parasitic diseases, neurologic and neuromuscular conditions, and viral conditions including AIDS.

33. The pharmaceutical composition in accordance with claim 32, wherein the medical conditions further include vasospasm, Parkinson's disease, Alzeihmer's disease, malaria, tuberculosis, arthritis, allergic and asthmatic conditions, hepatitis, coronary and peripheral vascular ischemia-reperfusion injury of blood vessels.

34. The pharmaceutical composition in accordance with claim 26, wherein the composition is orally formulated in combination with a liquid diluent or a solid carrier.

35. The pharmaceutical composition in accordance with claim 26, wherein the therapeutically effective dosage of the composition prevents the occurrence of, reduces the rate of growth of, or diminishes the size of tumor cells or any combination therof.

* * * * *